United States Patent [19]

Tabata et al.

[11] Patent Number: 5,744,381
[45] Date of Patent: Apr. 28, 1998

[54] METHOD OF INSPECTING A PATTERN FORMED ON A SAMPLE FOR A DEFECT, AND AN APPARATUS THEREOF

[75] Inventors: Mitsuo Tabata, Yokohama; Toru Tojo, Kanagawa-ken; Toshiyuki Watanabe, Yokohama; Hideo Tsuchiya, Kawasaki, all of Japan

[73] Assignee: Kabushiki Kaisha Toshiba, Kawasaki, Japan

[21] Appl. No.: 614,063

[22] Filed: Mar. 12, 1996

[30] Foreign Application Priority Data

Mar. 13, 1995 [JP] Japan ................................ 7-052947
Mar. 17, 1995 [JP] Japan ................................ 7-059265

[51] Int. Cl.$^6$ ........................ G01R 31/26; H01L 21/66; G03F 9/00; G01N 21/00
[52] U.S. Cl. ........................ 438/16; 430/5; 356/237; 382/144
[58] Field of Search ........................ 437/8; 356/237, 356/239; 382/144; 430/5; 438/16

[56] References Cited

U.S. PATENT DOCUMENTS

| | | | |
|---|---|---|---|
| 4,559,603 | 12/1985 | Yoshikiawa | 356/237 |
| 5,029,222 | 7/1991 | Yamada et al. | 382/144 |
| 5,068,799 | 11/1991 | Jarrett, Jr. | 356/239 |
| 5,379,348 | 1/1995 | Watanabe et al. | |
| 5,404,410 | 4/1995 | Tojo et al. | 382/144 |

OTHER PUBLICATIONS

SPIE, Photomask Technology and Management, vol. 2087, pp. 200–215, 1993, D.J. Stolpe, et al., "Die-to Die Inspection of Phase-Shifting Masks".

*Primary Examiner*—Brian Dutton
*Attorney, Agent, or Firm*—Oblon, Spivak, McClelland, Maier & Neustadt, P.C.

[57] ABSTRACT

A pattern defect inspection apparatus comprises a light irradiating portion, a light receive element, a light receive element amplifier, a preparation portion for preparing multivalued design pattern image data, an offset adjusting portion, a gain adjusting portion, and an inspecting portion. The offset adjusting portion adjusts the offset of the light receive element amplifier such that measurement data of a translucent portion of a pattern on a sample surface corresponds to design pattern image data corresponding to the translucent portion, regarding the translucent portion as a non-transparent portion. The gain adjusting portion adjusts the gain of the light receive element amplifier such that measurement data of a transparent portion of the pattern on the sample surface corresponds to design pattern image data corresponding to the transparent portion.

9 Claims, 15 Drawing Sheets

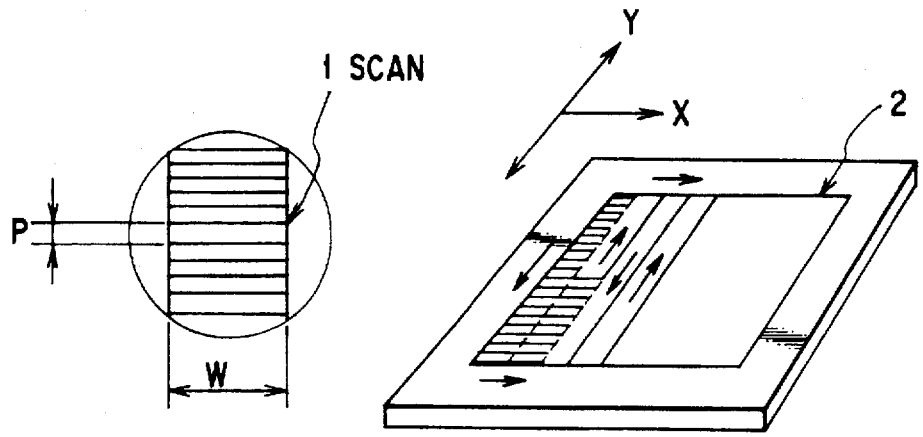
FIG. 1B
PRIOR ART
FIG. 1A
PRIOR ART
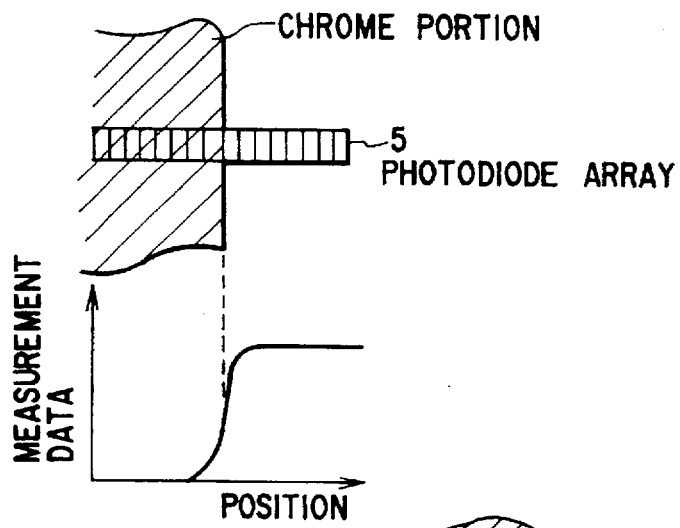
FIG. 3A
PRIOR ART
FIG. 3B
PRIOR ART
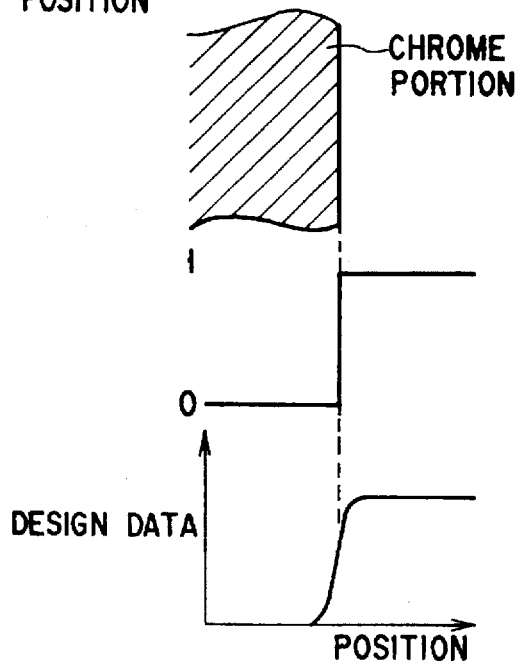
FIG. 4A
PRIOR ART
FIG. 4B
PRIOR ART

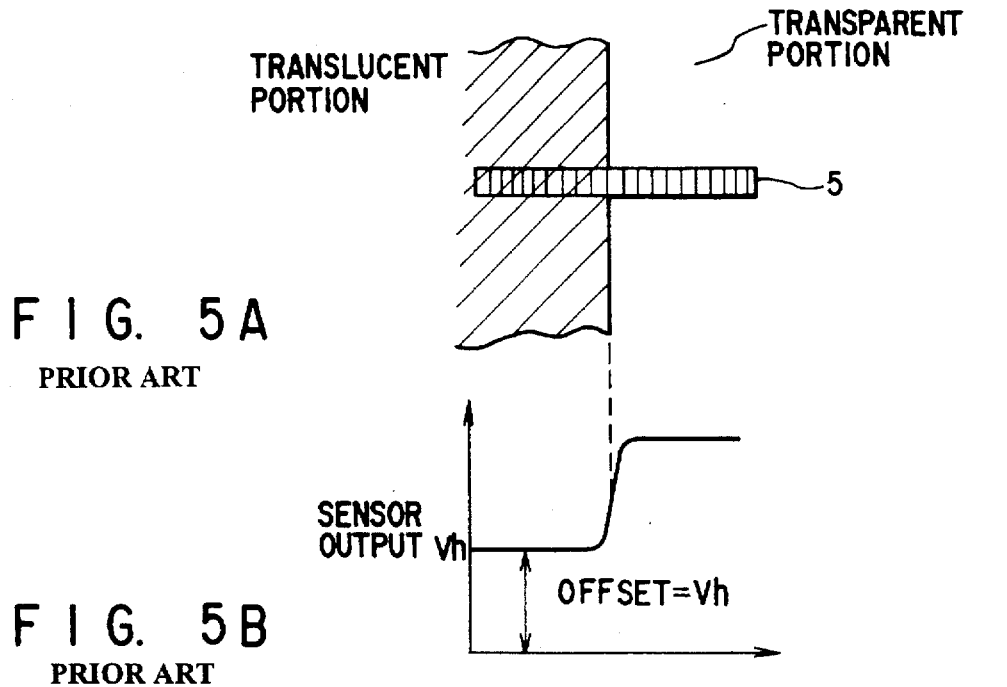
FIG. 5A PRIOR ART
FIG. 5B PRIOR ART
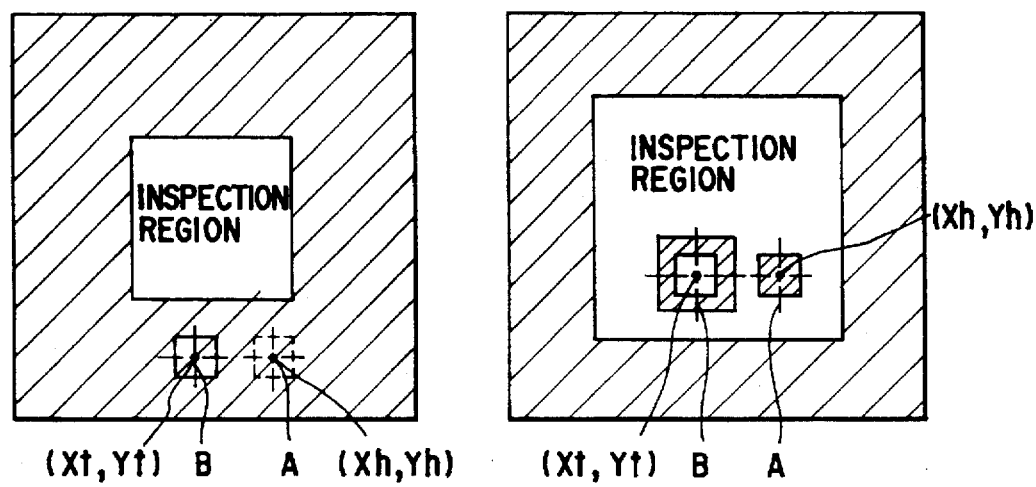
FIG. 6A PRIOR ART
FIG. 6B PRIOR ART
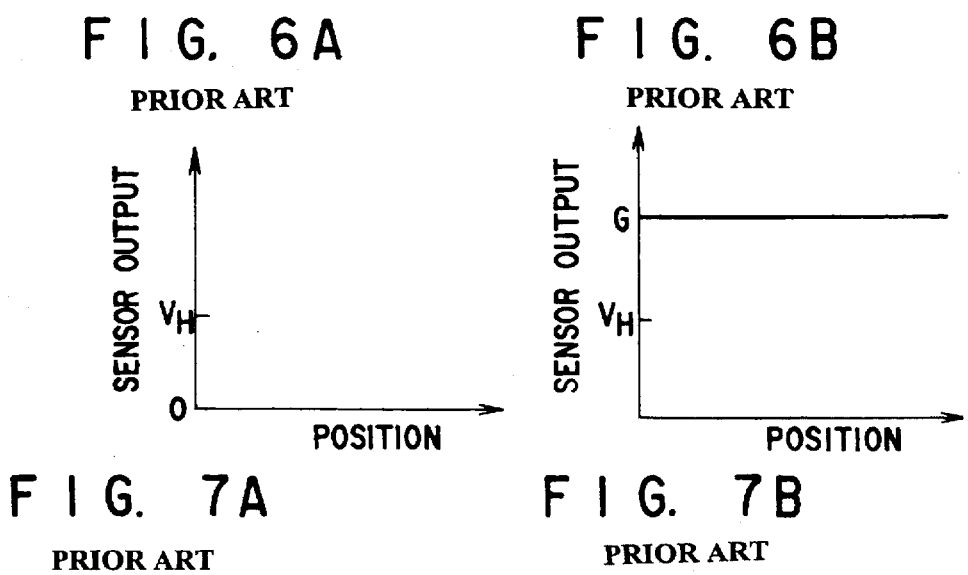
FIG. 7A PRIOR ART
FIG. 7B PRIOR ART

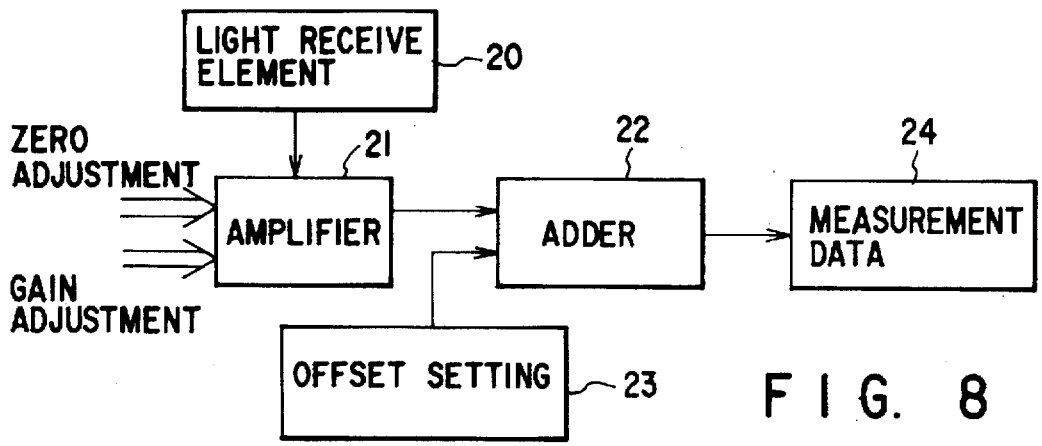
FIG. 8
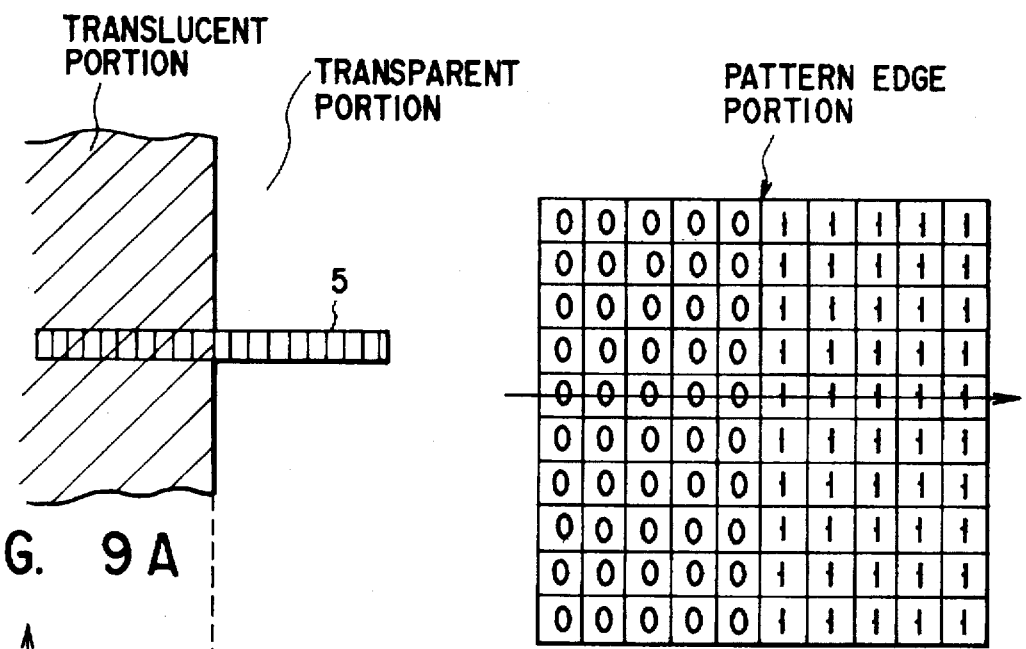
FIG. 9A
FIG. 9B
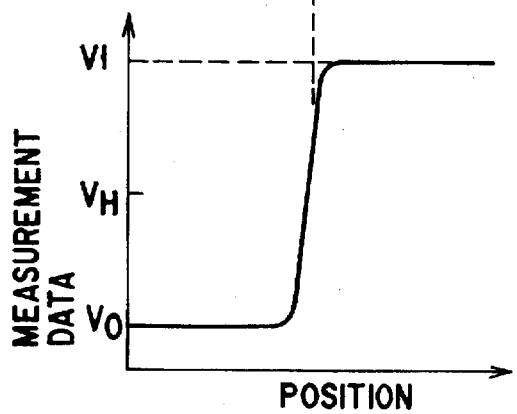
FIG. 10A
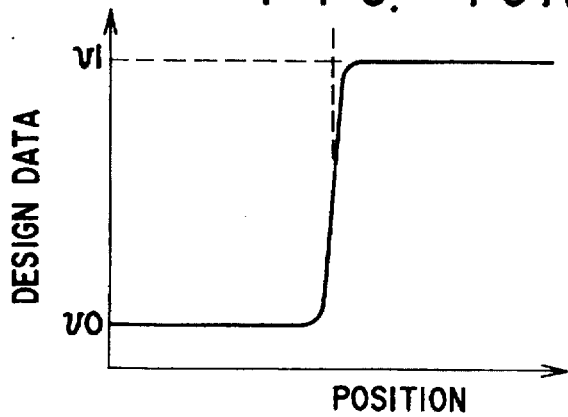
FIG. 10B

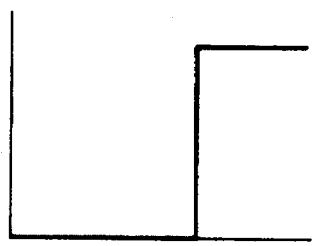
F I G. 15A
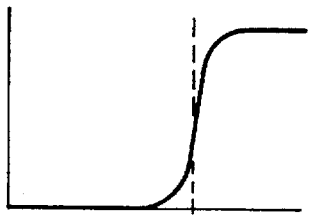
F I G. 15B
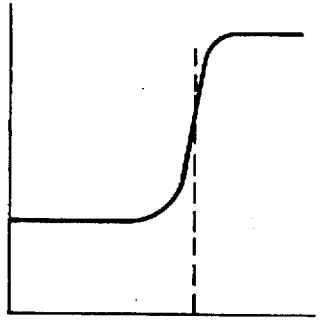
F I G. 15C
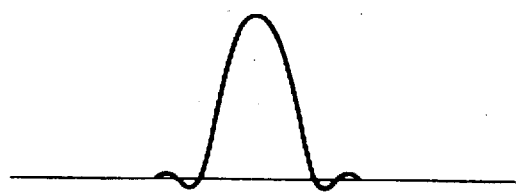
F I G. 17
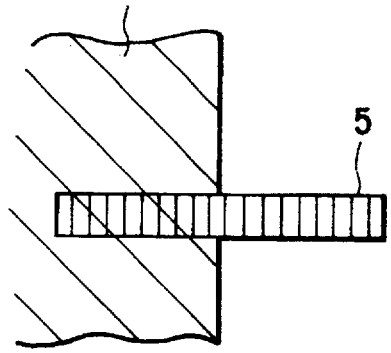
F I G. 16A
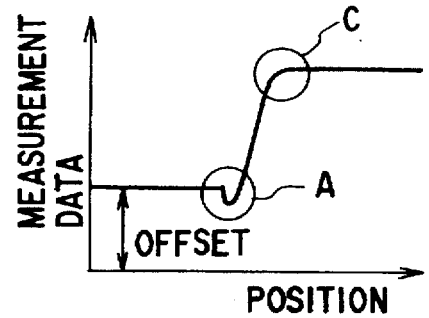
F I G. 16B
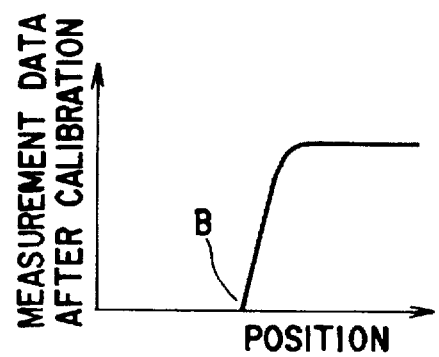
F I G. 16C

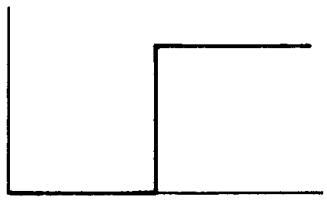
FIG. 18A — DESIGN DATA
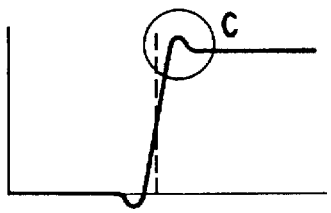
FIG. 18B — WAVEFORM PROCESSED WITH HALF-TONE MASK POINT EXPANSION FUNCTION
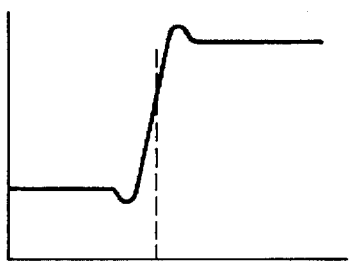
FIG. 18C — WAVEFORM AFTER ADDING OFFSET
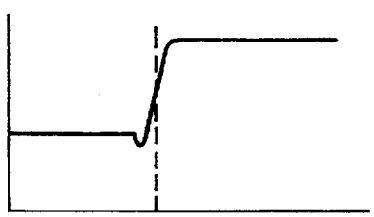
FIG. 18D — WAVEFORM AFTER AMPLITUDE LIMITATION
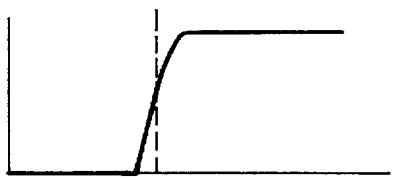
FIG. 20A — MEASUREMENT DATA AFTER CALIBRATION
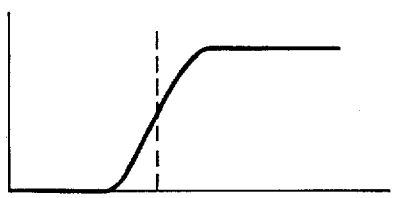
FIG. 20B — MEASUREMENT DATA AFTER FILTERING PROCESSING
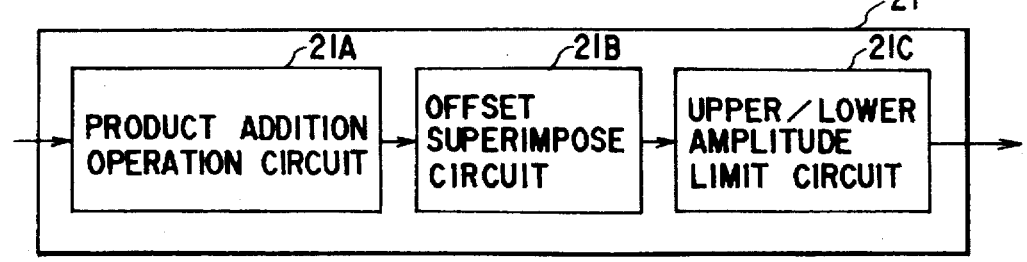
FIG. 19

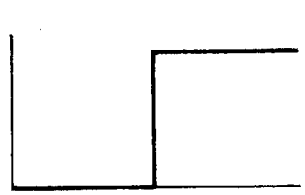
FIG. 21A  DESIGN DATA
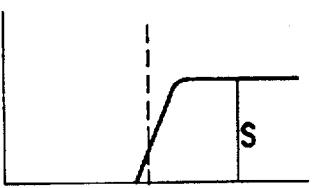
FIG. 21C  OFFSET SUBTRACTION  S
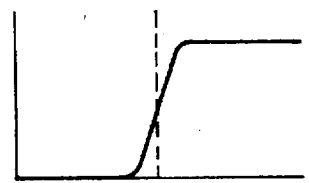
FIG. 21B  PROCESS WITH POINT EXPANSION FUNCTION
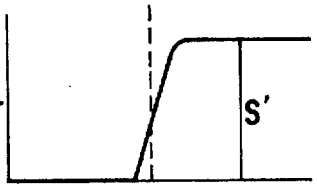
FIG. 21D  AMPLITUDE ADJUSTMENT  S'
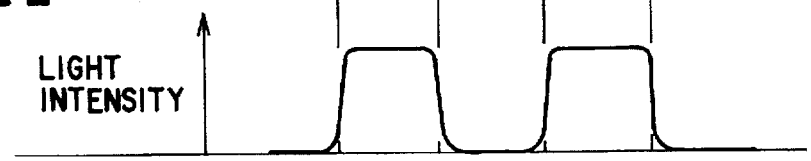
FIG. 22
LIGHT INTENSITY
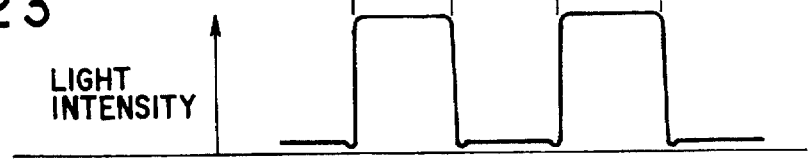
EXPOSURE LIGHT
FIG. 23
PHASE 0° SIDE LIGHT AMPLITUDE
PHASE 180° SIDE LIGHT AMPLITUDE
LIGHT INTENSITY

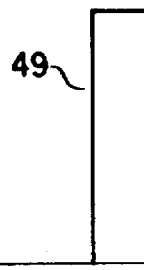
FIG. 29
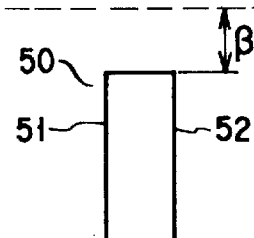
FIG. 32
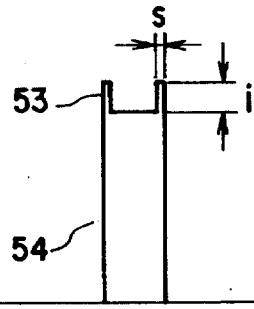
FIG. 30A
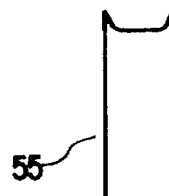
FIG. 30B
FIG. 30C
FIG. 30D
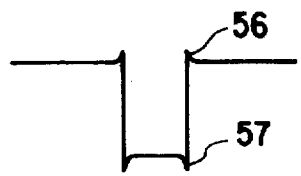
FIG. 31A
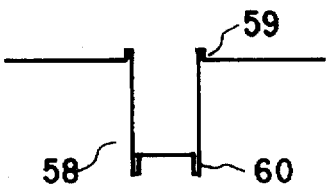
FIG. 31B

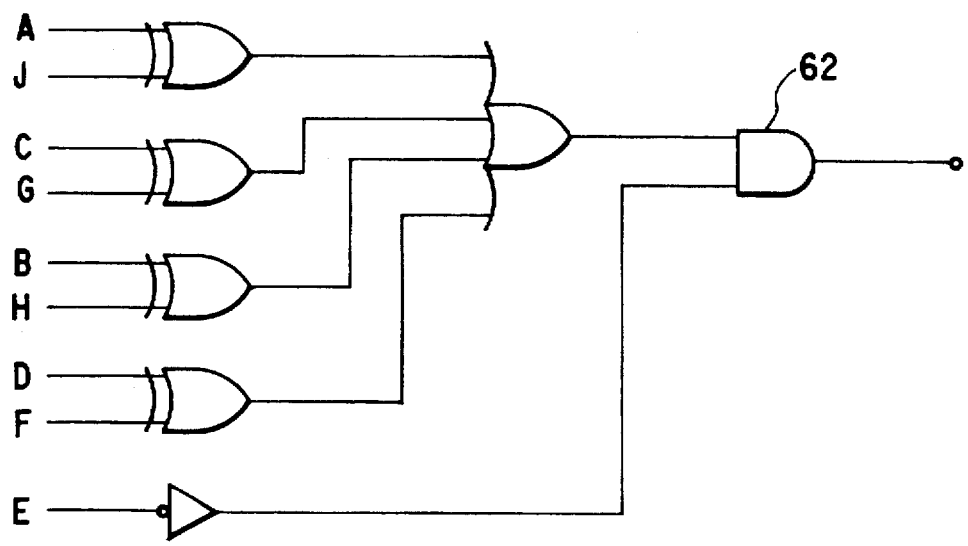
F I G. 33
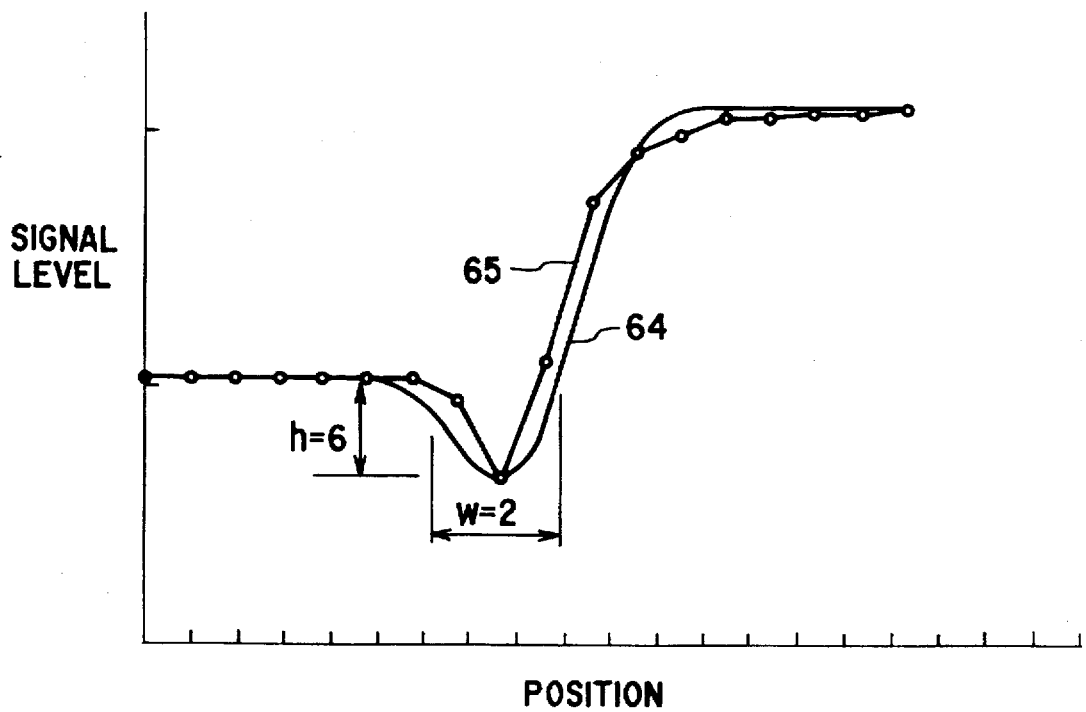
F I G. 34

METHOD OF INSPECTING A PATTERN FORMED ON A SAMPLE FOR A DEFECT, AND AN APPARATUS THEREOF

BACKGROUND OF THE INVENTION

1. Field of the Invention

The present invention relates to a method of inspecting a pattern formed on a sample, such as a photomask or the like, for a defect, and an apparatus thereof, particularly used for manufacturing semiconductors.

2. Description of the Related Art

One of significant factors which cause reductions in yield of manufacturing large scale integrated circuits (LSIs) is a defect occurring in a photomask or reticule used for manufacturing a device by a photolithography technique. To improve the yield, developments have eagerly been made to an apparatus for detecting such a defect and have been put into practical use.

Conventional mask defect inspection apparatuses can be roughly divided into two types respectively based on two methods. In one of the methods, two chips on each of which one same pattern is formed are respectively observed by individual detection means, and are compared with each other to detect any difference between both chips, by an appropriate defect detection means. In the other method, a chip with a pattern formed thereon is observed by a detection means, and is compared with design data of the pattern by an appropriate defect detection means, thereby to detect any defect. In the former method, since two chips on each of which one same pattern is formed are observed individually, defective portions cannot be detected if one same defective portion occurs on each of the chips. In the latter method, the pattern is compared with design data, and therefore, does not result in such a problem.

Examples of an apparatus which performs inspections with use of design data will be an apparatus taught in the reference (Super LSI High Accuracy Full Automatic Reticule Inspection Apparatus, Electronic Material, September 1983, pp. 47), a technique taught in Japanese Patent Application KOKAI Publication No. 1-40489, or the like. Design data used for preparing (or drawing) a reticule should desirably be the same as that inputted to a detection apparatus to perform an inspection. A drawing apparatus designed and manufactured on this conception can be paired with an inspection apparatus, to form an effective drawing/ inspecting system.

Most conventional masks to be inspected are formed by vapor-depositing non-transparent chrome on transparent glass, drawing a pattern thereon, and thereafter subjecting the glass to etching processing. These masks have an ideal characteristic that transmittances are substantially 100% and 0%. Meanwhile, the design data are originally formed of binary data expressed by 1 and 0, and therefore, measurement data obtained by a sensor element through an optical system can be relatively easily related to the design data.

In recent years, in order to improve the resolution characteristic of an exposure apparatus, various phase shift masks have been designed and practiced. Among these masks, a mask called a half-tone mask is expected as useful since it allows easy pattern designing. This half-tone mask uses a translucent film made of silicon nitride, MoSi or the like in place of a conventional chrome film.

Like other conventional chrome masks, this kind of mask must be subjected to a defect inspection with respect to a pattern formed with use of half-tone film.

However, a translucent film has a transmittance of about 10% to 70% or more in several cases, and therefore, achieves a low optical contrast. Therefore, sufficient defect inspections cannot be achieved with use of the half-tone mask.

Thus, in a conventional pattern defect inspection, it is difficult to detect fine small defects from a mask formed with use of a translucent film, such as a half-tone mask or the like, with a high accuracy.

The object of the present invention is to provide a pattern defect inspection method and an inspection apparatus with which fine small defects can be detected with a high degree of accuracy, from a mask made with use of a translucent film, such as a mask, like from a conventional chrome mask.

SUMMARY OF THE INVENTION

In order to achieve the above object, the present invention adopts the following structure.

In the present invention, when a half-tone mask is inspected, calibration processing is performed before the inspection, thereby to adjust the zero point and gain of the light receive element amplifier output, such that a translucent portion of a pattern formed on a sample surface is regarded as a non-transparent portion. Specifically, a translucent portion previously provided is illuminated, and an adjustment is performed such that the zero point of the light receive element amplifier output in this state is zero. Next, the transparent portion previously provided is illuminated, and another adjustment is performed such that the gain of the light receive element amplifier output in this state is the gain standard value.

As an inspection apparatus, an adjustment margin of the offset of the light receive element amplifier is reserved so that the light receive element amplifier output obtained when illuminating a translucent portion can be decreased to zero, while a gain margin of the light receive element amplifier is reserved so that the light receive element amplifier output obtained when illuminating the translucent portion can be increased to the gain standard point.

Next, a predetermined offset amount is added. The largest and smallest value of the output obtained as a result of adding the predetermined offset amount are respectively defined as the high level standard value and the low level standard value. These low and high level standard values are determined in compliance with the levels of the design data described below, as inspection comparison standard. Specifically, these values are made so as to correspond to the low level value and high level value multi-valued on the basis of binary data. Specifically, a translucent portion of a pattern is regarded as a non-transparent portion, and the sensor amplifier output is made so as to correspond to an output value of design design data corresponding to a non-transparent portion, with respect to the translucent portion. With respect to a transparent portion, the sensor amplifier output is made so as to correspond to an output value of design data corresponding to a transparent portion.

In this structure, a translucent portion on a sample surface of a half-tone mask can be taken as a non-transparent portion by performing calibration processing before performing an inspection, and therefore, observation data and design data can be made so as to substantially correspond to each other. In this manner, lack of correspondence between measurement data and design data which conventionally lies in case of a half-tone mask can be avoided, and an inspection can be achieved by comparing the measurement data and the design data, without causing false defects.

In addition, according to the present invention, consideration is taken into a factor which causes many false defects and prevents improvements in the detection sensitivity when inspecting a half-tone mask false defects lies in the output characteristic in an area of a pattern edge portion. Therefore, occurrence of false defects is prevented to a minimum level, by performing proper filter processing for making the output characteristics of design data and measurement data, so as to correspond to each other in an area of a pattern edge portion so as to correspond.

In the present invention, firstly, design data is subjected to an integration, convoluting a function incorporating a profile characteristic specific to a half-tone film. Secondly, measurement data is subjected to filter processing for smoothening sharp data changes. Thus, the present invention is essentially based on the concept of adding a means of performing proper filter processing on design data or measurement data, in order that the output characteristics of design data and measurement data correspond to each other at a pattern edge portion, in compliance with the characteristics of a mask to be inspected.

In this structure, output profiles of the pattern edges on design data and measurement data excellently correspond to each other, even in case of inspecting a half-tone mask, and occurrence of false defects can be prevented to a minimum level, so that the detection sensitivity can be increased. In this respect, conventional comparison algorithms can be directly used. In addition, even a half-tone mask having a specific characteristic can be treated by selecting a filter in compliance with the characteristic, so that a defect inspection apparatus can be provided more practically.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention and, together with the general description given above and the detailed description of the preferred embodiments given below, serve to explain the principles of the invention.

FIGS. 1A and 1B are views showing an example of a conventional inspection method adopted in a pattern defect inspection apparatus;

FIGS. 3A and 3B show measurement data at a conventional pattern edge portion in case of a chrome mask;

FIGS. 4A and 4B show design data and design conventional conventional pattern image data at a pattern edge portion;

FIGS. 5A and 5B show measurement data at a conventional pattern edge portion of a half-tone mask;

FIGS. 6A and 6B are views showing a half-tone calibration transparent region and a translucent region according to a conventional method;

FIGS. 7A and 7B are graphs showing a principle of conventional half-tone calibration;

FIG. 8 shows a circuit diagram for performing offset adder processing;

FIGS. 9A and 9B show measurement data at an edge portion of a half-tone pattern after calibration;

FIGS. 10A and 10B show design pattern image data at an edge portion of a half-tone pattern;

FIGS. 15A, 15B and 15C are graphs showing a waveform of design data, a waveform obtained by subjecting design data to a point expansion function, and a waveform obtained by further subjecting the waveform to offset addition;

FIGS. 16A, 16B, and 16C show measurement data and design data at a pattern edge portion of a half-tone mask;

FIG. 17 is a graph showing an example of a senile function of a half-tone mask;

FIGS. 18A, 18B, 18C, and 18D are graphs showing the concept for preparing inspection standard data for an half-tone mask from design data;

FIG. 19 is a block diagram showing an example of processing steps in a data conversion circuit;

FIGS. 20A and 20B are graphs showing examples of waveforms obtained by subjecting measurement data to filter processing;

FIGS. 21A, 21B, 21C, and 21D are graphs showing the concept for preparing inspection standard data from for a half-tone mask from design data;

FIG. 22 shows the concept for expressing a light intensity on a wafer when a Cr mask is transferred by a stepper;

FIG. 23 shows the concept for expressing a light intensity on a wafer when a phase shift mask is transferred by a stepper;

FIG. 29 shows an example of a filter used when performing filter processing on bit image data corrected and processed;

FIGS. 30A, 30B, 30C, and 30D schematically show a flow of processing on bit image data when the apparatus of the embodiment is used to perform an inspection in a reflection light detection system;

FIGS. 31A and 31B show an example of a detection signal expected when simultaneously using transmitted light and reflection light, and a bit image signal corresponding thereto;

FIG. 32 is a view for explaining a detection mask for detecting an edge of a pattern;

FIG. 33 is a logic circuit diagram for detecting an edge of a pattern; and

FIG. 34 is a graph showing a measurement signal detected when observing a phase shift mask, and a reference pattern data signal obtained by application of the present invention.

DETAILED DESCRIPTION OF THE PREFERRED EMBODIMENTS

In the following, embodiments of the present invention will be explained with reference to the drawings.

(Embodiment 1)

The following explanation will be made to a mask defect inspection apparatus for detecting a defect in a mask pattern, citing design data as an example. The basic structure of inspection of this kind is taught in the reference Super LSI High Accurate Full Automatic Inspection Apparatus, Electronic Material, September 1983, pp. 47. FIGS. 1A and 1B show an inspection method, and FIG. 2 shows an example of the structure of the apparatus.

As shown in FIGS. 1A and 1B, an inspection is performed by enlarging a mask pattern with use of an optical system, and sequentially observing narrow strip-like portions each having a width W=500 μm or so (e.g., a table is shifted sequentially by a length p).

Figure 2:
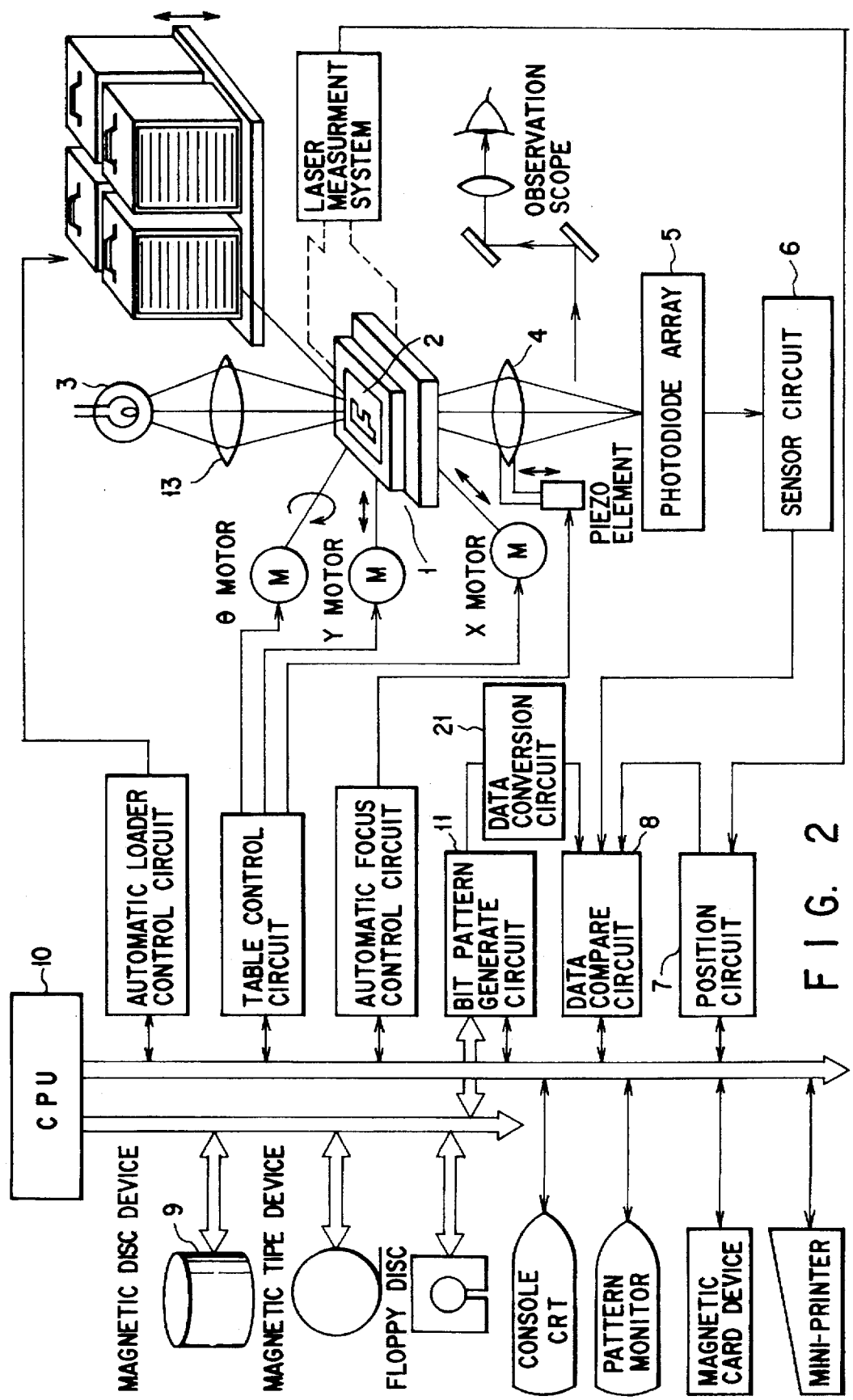
FIG. 2 shows a system structure of a pattern defect inspection apparatus according to a first embodiment.

As shown in FIG. 2, a mask 2 to be inspected is placed on an XYθ-table 1, and a pattern thereof is illuminated by a light source 3 and an illumination lens 13. An objective lens 4 is used to form a pattern image on a photodiode array (or light receive element) 5, thereby to obtain measurement subjected to data A/D conversion by a sensor circuit 6 consisting of a sensor amplifier portion and an A/D conversion portion. This measurement data together with position data from a position circuit 7 are supplied to a data comparison circuit 8. Meanwhile, design data of a pattern is supplied from a magnetic disc device 9 through a control calculator (or CPU) 10 to a bit pattern generator circuit (or data developing circuit) 11. Then, figure data is converted into binary data and supplied a data conversion circuit 21.

In the data conversion circuit 21, binary bit pattern data is subjected to an integration convoluting a point expansion function equivalent to the optical system, thereby to prepare multi-valued pattern image data. This means, since a low pass filter on a spacial frequency is kept effected due to the resolution characteristic of the objective lens 4 and the aperture effect of the photodiode array 5, filter processing is performed on design data, thereby to imitate ideal measurement data.

Both data are compared with each other in accordance with a proper algorithm by a data comparison circuit 8, and such a portion which leads to lack of correspondence between the design pattern image data and the measurement data is determined as a defect. For example, this algorithm will be a method of directly comparing both data with each other, or a method of making a comparison by obtaining differentiated values (or gradient vectors) of the pattern data, as disclosed in Japanese Patent Application KOKAI Publication No. 62-266406.

In these inspection methods, a chrome mask pattern is actually measured as shown in FIG. 3A. Then, the output from the light receive element forms a waveform of a pattern having a vague edge as shown in FIG. 3B, due to the resolution characteristic of the objective lens 4 and the aperture effect of the photodiode array 5, as has been described above. Meanwhile, the design pattern image data obtained by subjecting the design data as shown in FIG. 4A to filter processing forms a waveform similar to the measurement data as shown in FIG. 4B. Thus, by comparing design pattern image data with measurement data in accordance with a proper algorithm, a fine small defect can be detected with a high accuracy. The procedures of this filter processing can be carried out by a method disclosed in, for example, Japanese Patent Application KOKOKU Publication 63-3450.

Meanwhile, in the case of inspecting a half-tone mask as shown in FIG. 5A, the output of the light receive element forms a waveform increased by an offset Vh as shown in FIG. 5B, and thus does not correspond to the design pattern image data shown in FIG. 4B. Therefore, even when there are no defects, many false defects appear due to lack of correspondence between data if defect detection is carried out in a manner similar to a conventional method. Thus, a comparison inspection is not possible in this case.

Hence, in this embodiment, when inspecting a half-tone mask, half-tone calibration processing as will be described below is performed before carrying out an inspection, so as to achieve an inspection with a high accuracy, while reducing false defect occurrence.

At first, as a prerequisite, a translucent region A and a transparent region B are previously provided on a half-tone mask to be inspected, as shown in FIGS. 6A and 6B. The translucent region A and the transparent region B may be out of an inspection region, as shown in FIG. 6A, or may be within the inspection region as shown in FIG. 6B. Both of the regions A and B are each set to a size sufficiently larger than the size of a light receive element, when projected onto the receive element through the regions on the mask.

Note that in the case where these regions cannot be provided on a mask to be inspected, a calibration mask provided with a translucent region and a transparent region may be previously prepared. In this case, the characteristic of the half-tone film of the calibration mask is arranged so as to correspond to the characteristic of a mask to be inspected. The layout coordinates (Xh, Yh) of the translucent region A on the mask as well as the layout coordinates (Xt, Yt) of the transparent region B of the transparent region B on the mask must be predetermined.

Conventionally, a sensor amplifier is adjusted such that the output is 0 with respect to a non-transmitting portion which is not irradiated with light and that the output is maximum value Vmax or approximated thereto with respect to a transmit portion which is most intensively irradiated with light. Therefore, where calibration processing is not performed, the sensor amplifier output obtained through a translucent portion such as a half-tone film is an intermediate value Vh between 0 and Vmax, and the output forms a waveform as shown in FIG. 5B, with respect to a pattern edge portion of the half-tone film.

Therefore, the following calibration processing is performed. At first, the translucent portion as described above is irradiated with light, and XYθ-table is moved such that the translucent portion is projected on the light receive element through the region. In this state, the stopping position of the table may be determined on the basis of the layout coordinates (Xh, Yh). As shown in FIG. 7A, the sensor amplifier output is adjusted such that the sensor amplifier output obtained at this time is 0. The inspection apparatus may be arranged so as to have a sufficient adjustment margin for the offset of the sensor amplifier, so that the sensor amplifier output obtained when illuminating a translucent portion can be decreased to 0.

Next, the transparent portion is irradiated with light, and the table is moved such that the transparent portion is projected through the region onto the light receive element. As shown in FIG. 7B, the gain in the sensor amplifier side is adjusted such that the sensor amplifier output obtained at this time can be a predetermined gain standard value G. The inspection apparatus is arranged so as to have a gain margin of the sensor amplifier, so that the sensor amplifier output obtained when illuminating the transparent portion can be increased to a gain standard value G.

Further, a constant offset (V0) is added to the amplifier output and is defined as measurement data. In this case, the circuit configuration comprises a light receive element 20, an amplifier 21, an adder 22, offset setting 23, and obtaining 24 of measurement data. As a result of this, after calibration processing, the measurement data obtained through a translucent pattern edge portion is as shown in FIG. 9B. In this case, the level of the output from a translucent portion of the measurement data is the low level standard value (V0), while the level of the output from a transparent portion is the high level standard value (V1).

The low level standard value and the high level standard value as described above are determined in compliance with the levels of design data which serve as inspection comparison standards described later. Specifically, design data at a pattern edge portion as shown in FIG. 10A forms a multi-valued waveform (or design pattern image data) which reflects vagueness of an optical system, due to a convoluting integration (or product/addition operation). This method of convoluting integration may be, for example, the method taught in Japanese Patent Application KOKOKU Publication 1-40489.

Here, the low level value V0 and the high level value V1 of the design pattern image data can be made so as to respectively correspond to the low level standard value V0 and the high level standard value V1 of the sensor amplifier output, by coefficients used in the operation and offset addition processing. Specifically, with a translucent portion of a pattern regarded as a non-transparent portion, the sensor amplifier output can be made so as to correspond to the output value of the design pattern image data corresponding to the non-transparent portion. With respect to a transparent portion, the sensor amplifier output is made so as to directly correspond to the output value of design pattern image data corresponding to a transparent portion. As a result of this, for example, the sensor output at an edge portion of a half-tone pattern and the output value of the design data are expressed as shown in FIGS. 9B and 10B, and can thus be made so as to substantially correspond to each other.

Figure 11:
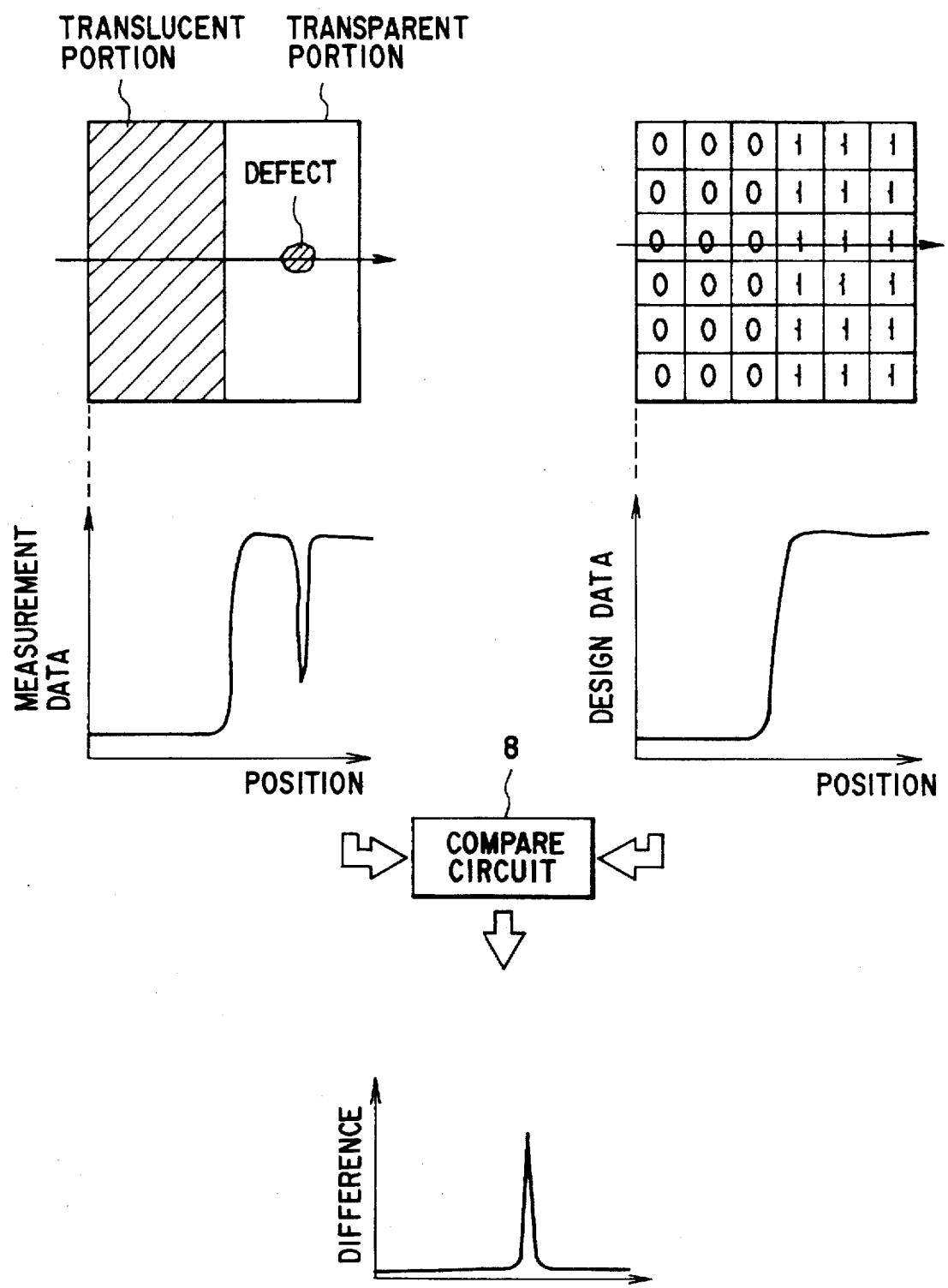
FIG. 11 shows a defect detection principle used when a defect exists in a half-tone pattern.

If an inspection is carried out after the half-tone calibration processing as described above is performed, a translucent portion of a pattern can be regarded as a non-transparent portion, and the sensor output of the half-tone pattern can be made so as to correspond to the output of the design data. As a result of this, as shown in FIG. 11, when there is a defect in a half-tone pattern, a difference appears between the measurement data and the design pattern image data, and therefore, the defect can be detected by a data comparison circuit 8 with a high accuracy like in a case of inspecting a chrome pattern. In this case, a method of directly comparing data with each other, or a method of comparing data with each other by obtaining differentiated values (or gradient vectors) can be used as a comparison algorithm, and thus, methods similar to the conventional methods can be adopted.

Figure 12A:
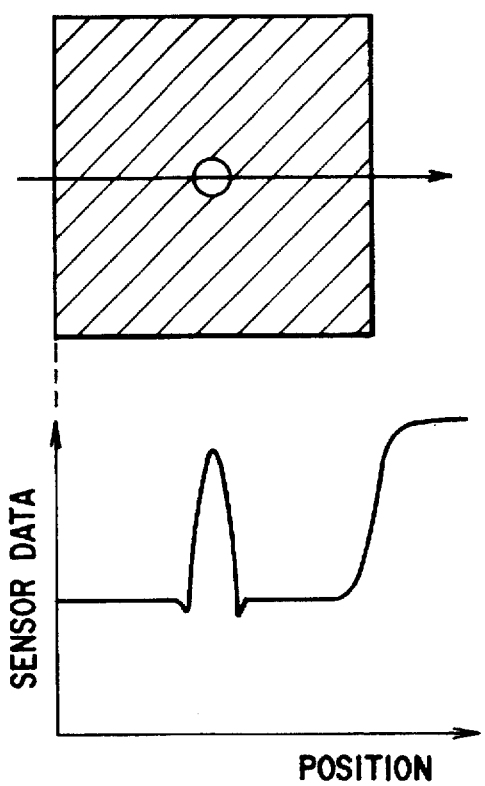
FIGS. 12A and 12B show a sensor output when a pin-hole defect exists in a half-tone pattern.
Figure 12B:
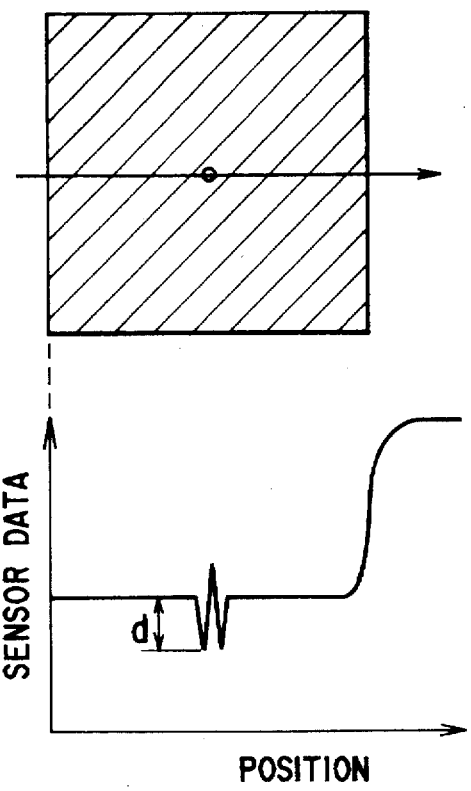

Note that the low level standard value V0 is normally be set to 0, in order to ensure a dynamic range for signals and facilitate the gain adjustment of the amplifier. However, the present inventors have found that a novel effect can be obtained if a certain constant value is added. Specifically, the waveform of a defect signal of a pin-hole like defect in a half-tone pattern changes in the following manner. As shown in FIG. 12A, if the size of the pin-hole like defect is relatively large, the positive signal (i.e., a signal appearing in the plus side of the half-tone level) obtained by light passing through the pin-hole is large. On the contrary, as shown in FIG. 12B, if the size of the defect is fine and small, e.g., 1 μm or less, the positive signal obtained by light passing through the pin-hole is small. However, the waveform at an edge portion of a defect appears in the minus side of the half-tone level (as a negative signal), due to a phase shift effect, and the size is larger than the signal appearing in the plus side.

Figure 13A:
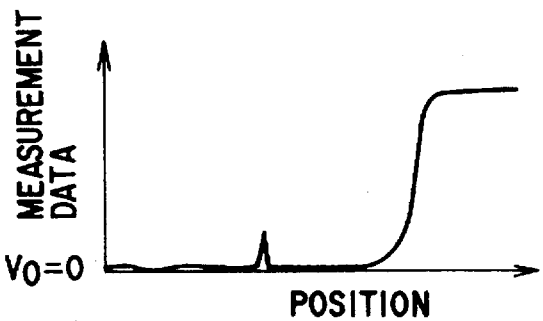
FIGS. 13A and 13B show measurement data of a pin-hole defect in a half-tone pattern after calibration.
Figure 13B:
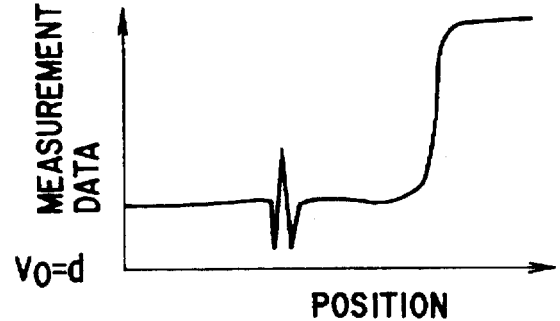

Therefore, measurement data includes only positive signals where V0=0 exists, as shown in FIG. 13A, so that fine defects are detected with difficulty. Consequently, a constant value is added with a value d which is greater than the signal amplitude appearing in the minus side during calibration (V0=d), and as a result, the negative signal at the edge portion is directly stored, as shown in FIG. 13B.

Figure 14:
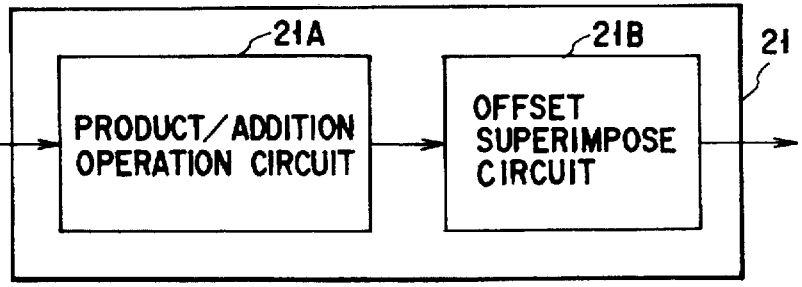
FIG. 14 is a circuit diagram of a data conversion circuit when offset addition is performed on design data.

Meanwhile, a waveform processed with a point expansion function as shown in FIG. 15B as well as a waveform superimposed by an offset as shown in FIG. 15C are obtained from the design data shown in FIG. 15A, if the data conversion circuit 21 is constructed by a product/addition circuit 21A and an offset superimpose circuit 21B as shown in FIG. 14. Therefore, if FIGS. 13B and 15C are compared with each other, a negative signal at a defect edge portion directly appears as a difference therebetween, so that a defect of a small size that cannot be detected by conventional methods can be detected. Thus, the defect detection ability is more improved.

Note that the present invention is not limited to the embodiments described above. The above embodiment relates to a mask defect inspection apparatus called a normal data base compare type which detects a defect in a mask pattern with use of design data. Otherwise, the present invention may be of a mask defect inspection apparatus called a die-to-die compare type in which two chips having one same pattern drawn thereon are respectively observed by individual detection means, and both of the chips are compared with each other, thereby to detect a difference therebetween by an appropriate defect detection means. In this case, measurement data is obtained by two sensor amplifiers, and the same effects can be obtained by performing calibration processing described above on the outputs of the two amplifiers. In addition, this embodiment can be variously modified and practiced without deviating from the subject matter of the present invention.

(Embodiment 2)

A second embodiment of the present invention will be explained next. The basic structure of the mask defect inspection apparatus of this embodiment is the same as that of the first embodiment, and detailed explanation thereof will be omitted herefrom.

When inspecting a half-tone mask as shown in FIG. 16A, the output of the photodiode array 5 has a waveform superimposed by an offset, as shown in FIG. 16B, and does not correspond to the design data as shown in FIG. 4B, so that false defects frequently occur and the detection sensitivity cannot be increased so much as in the case of a chrome mask.

The present inventors have made eager studies in this respect, and have found that the output drops at a pattern edge portion in case of an half-tone mask (e.g., the portion A in FIG. 16B), and this drop makes the profile of measurement data different from the characteristic obtained by the resolution characteristic of an objective lens 4 or the aperture effect of the photodiode array 5. The second embodiment and a third embodiment, to be explained later, solve the above problem.

In the second embodiment, when design data is subjected to filter processing thereby to imitate ideal measurement data, in the data conversion circuit 21, product/addition operation is performed convoluting a function including a profile characteristic specific to a half-tone film.

This function is obtained by estimating a point expansion function for a half-tone film from an edge profile (FIG. 16B) between a half-tone film and a glass portion. Otherwise, the estimation method will be a method in which various grid patterns at predetermined intervals are observed, and a spacial frequency characteristic is obtained therefrom, which is subjected to Fourier transformation.

In any of those methods, the point expansion function for a half-tone mask indicates a characteristic with references (including minus coefficient items), as shown in FIG. 17. The design data as shown in FIG. 18A is subjected to a product/addition operation convoluting the point expansion function for the half-tone mask, by the data conversion circuit 21, thereby to obtain an expectation value of the measurement data, as shown in FIG. 18B. Further, in order to approximate the expectation value to actual measurement data, an offset amount is added, the signal amplitude is adjusted, and a signal limiter is activated.

In an offset means and a signal amplitude adjustment means, a light amount value equivalent to a translucent portion of a half-tone film is added as an offset to the waveform of FIG. 18B, in order that the data complies with the waveform of FIG. 16B of the measurement data, and the amplitude is adjusted to make the light amount value correspond to a glass portion. In this manner, the waveform shown in FIG. 18C is obtained.

A limiter means is provided to process the portion C of the waveform shown in FIG. 18B into a flat shape. Actual measurement data of the half-tone mask does not cause overshooting at the portion C, as shown in FIG. 16B, but changes smoothly. Therefore, there may be a case that the limiter means must not only cut the waveform at a threshold value, but also simultaneously slightly activate a low pass filter on the spacial frequency. Presence or absence of overshooting is considered as being caused by saturation of photoelectric conversion on the photodiode array, the limiter need not be activated in several conditions.

Specifically, the internal structure of the data conversion circuit 21 is constituted by a product/addition operation circuit 21A as shown in FIG. 19, an offsets superimpose circuit 21B, and an amplitude adjustment and limiter circuit 21C. However, in general, superimposing of an offset and adjustment of the amplitude can be performed as batch-processing by selecting an appropriate coefficient in the product/addition operation.

The data conversion circuit 21 need not have the various means described above. Rather, in the circuit 21, input-output functions of the type described above may be provided in the form of a table of samples, and any input-output functions found optimal to masks which will be tested by simulation are selected and utilized. In this case, too, the same advantages can be attained.

In any of these means, standard data obtained from design data reflects a profile characteristic specific to a half-tone film, and therefore, design data to be compared is approximated to the profile of measurement data, as shown in FIG. 18D. As a result of this, occurrence of false defects can be prevented and minimized in the case of a half-tone mask, so that the detection sensitivity can be increased and fine small defects can be detected.

(Embodiment 3)

A third embodiment relates to a method in which measurement data is subjected to filter processing, thereby smoothing an edge portion, and comparison in a compare circuit 8 is carried out by a chrome mask. Measurement data of a conventional half-tone mask includes a sharp rise at the portion B of the waveform obtained by removing an offset portion, as is shown in FIG. 16C.

Here, filter processing for smoothing the waveform is performed by an added filter circuit, and further, the signal amplitude is amplified to be substantially equivalent to that of a chrome mask. In the data compare circuit 8, comparison with inspection standard data (or design pattern image data) for a chrome mask, as shown in FIG. 4B, is performed.

The filter circuit may be a digital filter as disclosed in Japanese Patent Application KOKAI Publication No. 03-124052. The characteristic of the filter is arranged such that the frequency characteristic is obtained so as to smooth the edge portion, and Fourier conversion is performed to obtain a filter function, contrary to the second embodiment.

By properly selecting the characteristic of the filter, the waveform of FIG. 16B, not FIG. 16C, can be inputted as measurement data to be processed by the filter means. This means, the same effects can be obtained when the order of the offset and amplitude adjustment means for the measurement data and the filter means is reversed.

As in the second embodiment, this filter means may be previously provided with samples of functions as described above, and a suitable one of the samples may be selected and used in compliance with a mask to be inspected by a simulation. Then, the measurement data after calibration will be as shown in FIG. 20A, and further, the measurement data after filter processing in which undershooting and sharp changes near an edge portion are smoothed, so that the measurement data is approximated to the profile of the design data shown in FIG. 4B. As a result of this, occurrence of false defects can be reduced to a minimum level in case of a half-tone mask, so that the detection sensitivity can be increased and fine small defects can be detected.

(Embodiment 4)

In a fourth embodiment of the present invention, it is proposed that the processing in the data conversion circuit 21 is changed and data comparison in the compare circuit 8 is performed in a different method. This is a method in which measurement data is processed by reducing the offset such that the measurement data value at a translucent portion of a half-tone film is zero as shown in FIG. 16C, and by performing calibration processing such that the dynamic range S is enhanced to S', and in which the inspection standard data obtained from design data is then approximated to the processed measurement data.

The procedures of this method are shown in FIG. 21. Specifically, design data shown in FIG. 21A is multiplied by a proper point distribution function by the product/addition operation means of the data conversion circuit 21, thereby to obtain data shown in FIG. 21B. Further, in order to make a sharp change at the portion B of FIG. 16C, an offset subtraction is slightly performed, thereby to obtain data shown in FIG. 16C. Then, data shown in FIG. 21D is obtained by adjusting the amplitude so as to compensate for this offset subtraction portion. Processing of measurement data is performed as shown in FIG. 16C, like in a conventional example.

By the processing described above, in the compare circuit, comparison can be performed between two items of data which sufficiently correspond to each other and have sharp rises at edge portions, as shown in FIG. 16C and FIG. 21D. As a result of this, it is possible to reduce occurrence of false defects to a minimum level in case of a half-tone mask, and the detection sensitivity can be increased, so that fine small defects can be detected.

As has been explained above, like in the second and third embodiments, either measurement data or design pattern image data inputted into the data compare circuit 8 can effectively be subjected to signal correction processing. Further, as explained in the fourth embodiment, both of the data can be processed together. In this case, conventional algorithms may be used. Even when there are half-tone masks having characteristics different from each other, the control calculator 19 can perform control such that optimal filters are respectively selected in accordance with the characteristics, thus achieving high usability.

Note that functions and filters which are prepared previously may be substituted by several coefficients, which may be arranged selectively or arbitrarily set. The selection and setting of these coefficients may be locally performed within the data conversion circuit 21 or the filter circuit 22, or otherwise may be performed by the control calculator 19. The latter case may be arranged such that optimal function or filter coefficients can further be obtained.

Further, the filter means and the offset means may be prepared in the form of a product/addition operation circuit and a numerical value operation circuit which satisfy necessary definitions. Otherwise, these means may be installed in the apparatus in the form of a function ROM (Read Only Memory) means including several variations which are previously calculated by a means such as a simulation, and a circuit is arranged such that the same effects can be achieved only by reading data from the ROM means in a reference table method.

As has been explained above, according to the present invention, in an inspection of a half-tone mask, calibration processing is performed to adjust the offset and gain of the sensor amplifier output, regarding a translucent portion of a pattern on a sample surface as a non-transparent portion, before performing an inspection, so that measurement data is made so as to substantially correspond to design data. Accordingly, the measurement data and the design data are compared with each other, with use of detection algorithms similar to conventional detection algorithms, and defects in a half-tone mask, which cannot be detected in a conventional method, can be detected.

As a result of this, even when a half-tone mask is used for manufacturing LSIs, defects of a shape of a pattern formed in a half-tone can be detected at a high level of accuracy, so that a decrease in the manufacturing yield in photolithography steps can be prevented. Therefore, manufacturing costs of LSIs can be reduced with great advantages.

In addition, according to the present invention, in an inspection of a half-tone mask, by performing appropriate filter processing in order that the output characteristics of design data and measurement data at a pattern edge portion are made so as to correspond to each other, occurrence of false defects can be reduced to a minimum level, so that the detection sensitivity can thus be improved. As a result, the defect detection sensitivity which is the most significant property for an inspection apparatus can be improved. Accordingly, a fine small defect which cannot be detected by a conventional method can be detected from a half-tone mask. In addition, since an optimal filter can be selected every time when the kind of a half-tone film is changed, the present invention is very effective for an inspection of a half-tone mask.

The present invention as has been described above and explained with reference to FIGS. 1 to 21, relates to a method and apparatus in which calibration processing for adjusting the offset and gain of the sensor amplifier output is performed, regarding a translucent portion of a pattern on a sample surface as a non-transparent portion, before performing an inspection of a half-tone mask. According to this method and apparatus, measurement data and design data are made so as to substantially correspond to each other. Therefore, the measurement data is compared with the design data with use of detection algorithms similar to conventional algorithms, thereby performing an inspection, and defects which cannot be detected by a conventional method can be detected from a half-tone mask.

However, in these method and apparatus, false defects may easily occur at a pattern edge portion. In the following, another inventive concept will be explained which is additionally applicable to the method and apparatus according to the present invention explained above and directed to FIGS. 1 to 21. At first, as a prerequisite of the following inventive concept, explanation will be mainly made to an example in which a sample such as a phase shift mask provided with a phase shifter portion is subjected to a defect inspection in a die-to-database inspection method.

In the case of inspecting a pattern of a phase shift mask by means of a pattern defect inspection apparatus, it is required to accurately detect a defect much finer and smaller than a defect of a Cr mask.

However, in a pattern defect inspection apparatus adopting the die-to-database inspection method, a measurement signal obtained by observing a phase shift mask is changed much more in comparison with a measurement signal obtained when observing a Cr mask, resulting in a problem that the detection sensitivity is lowered.

In general, the inspection wavelength used in a pattern defect detection apparatus is often different from the exposure wavelength of an exposure apparatus using a phase shift mask. In the case where a phase shift mask is illuminated with those different wavelengths and light passing through the phase shift mask is observed, the transmittance at a light shading portion of the phase shift mask is increased to be high, and a signal which is of zero level in case of a Cr mask floats up. Further, since the light passing through the light shading portion and the light passing through a transparent portion of glass as a substrate have phases different from each other, the signal causes undershooting at the boundary therebetween. This phenomenon occurs in an optical system of a pattern defect inspection apparatus, and this information is not included in the design pattern data used for preparing a pattern of the phase shift mask. Therefore, in the die-to-database inspection method in which the measurement data and the design pattern data are compared with each other to detect a defect, a large difference appears between the design data and the measurement pattern data, so that defects cannot be detected with a high sensitivity.

This phenomenon will be explained in more detail, with reference to FIGS. 22 to 25A and 25B.

FIG. 22 shows a Cr mask 23 formed of a glass substrate 21 on which a Cr pattern portion 22 is provided. Also, FIG. 23 shows a phase shift mask 26 formed of a glass substrate 24 on which a half-tone type phase shifter portion 25 is provided. In a normal Cr mask, a phase shift mask 26 provided with a phase shifter portion 25 corresponds to a Cr pattern portion. Note that the structure of a phase shift mask may adopt various methods. However, a phase shift mask 26 of a half-tone type will be explained to simplify the following explanation.

In this phase shift mask 26 of a half-tone type, a phase shifter portion 25 allows some percent of exposure light to pass, with respect to the wavelength of the exposure light, and the phase of the passing light is inverted by 180° in relation to the light passing through the glass substrate 24. Therefore, compared with the Cr mask 23 shown in FIG. 22, the transferred pattern of the phase shift mask 26 of a half-tone type achieves a higher resolution characteristic. Specifically, a condition wherein phases of adjacent light fluxes or phases in vicinities adjacent to each other are inverted to each other can be prepared with respect to wavelength of the exposure light, and therefore, the pattern resolution characteristic can be improved.

When this phase shift mask 26 is inspected by a pattern defect inspection apparatus adopting a die-to-database inspection method, the inspection is generally performed with use of light having a wavelength different from that of the exposure light, as explained above. In case of the Cr mask 23 shown in FIG. 22, since the Cr pattern portion 22 serves to shield light, there is no problem if the wavelength of exposure light is different from that of light used for the inspection. This means signals observed are not greatly changed depending on wavelengths.

However, in case of a phase shift mask 26, although the transmittance and the phase inversion at the phase shifter portion 25 are previously set with respect to the exposure wavelength, the transmittance and the phase inversion are not controlled with respect to the other wavelengths. For example, there is a case in which a phase shifter portion 25 attains a transmittance of some percent with respect to the exposure light wavelength, but attains several tens percent with respect to the wavelength of the inspection light. This increase in transmittance cannot be processed by inspection algorithms of a conventional pattern defect inspection apparatus adopting the die-to-database inspection method, and therefore, inspections cannot be achieved at a high sensitivity.

Figure 24A:
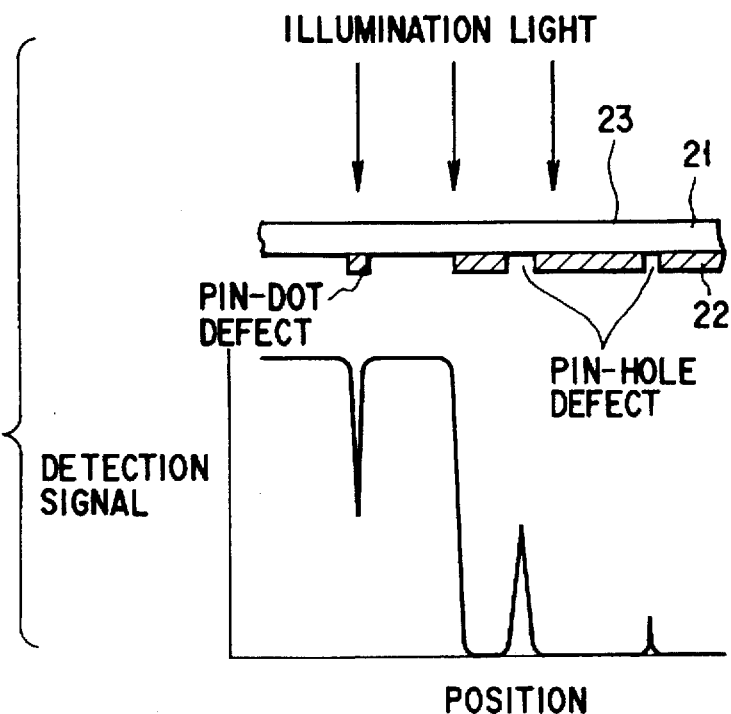
FIGS. 24A and 24B are views for explaining a detection signal obtained when observing a Cr mask by a transmitted light detection system, with use of a pattern defect inspection apparatus, and a detection signal obtained when observing a phase shift mask.
Figure 24B:
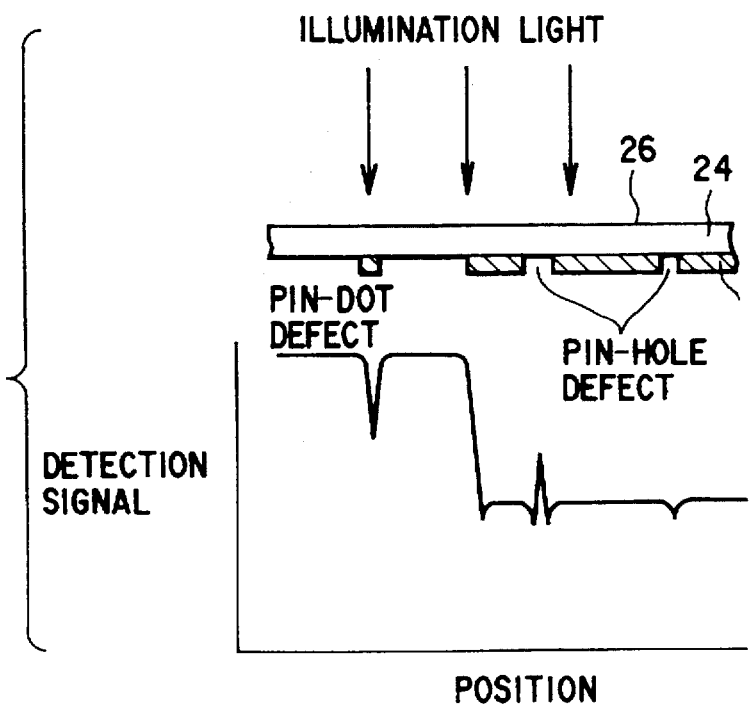

FIGS. 24A and 24B show detection signals actually obtained when observing transmitted light passing through a Cr mask 23 and a phase shift mask 26 each having pin-hole defects and a pin-dot defect, illuminated with light of a wavelength different from the wavelength of the exposure light. As is apparent from this observation example, the signal level at the phase shifter portion 25 corresponding to a light shielding portion is increased in the phase shift mask 26, and undershooting occurs at the edge portion.

Figure 25A:
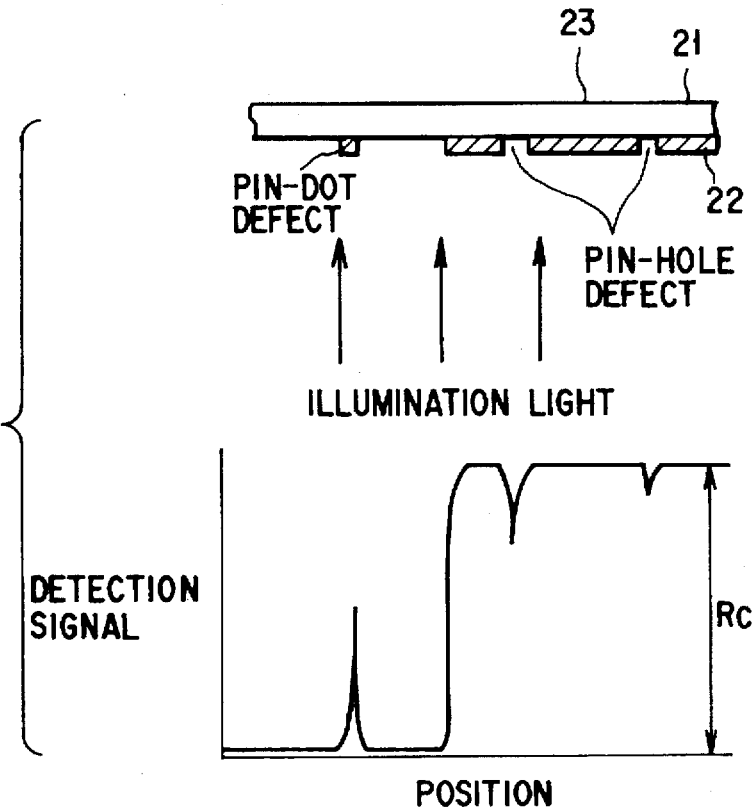
FIGS. 25A and 25B are views for explaining a detection signal obtained when observing a Cr mask by a reflection light detection system, with use of a pattern defect inspection apparatus, and a detection signal obtained when observing a phase shift mask.
Figure 25B:
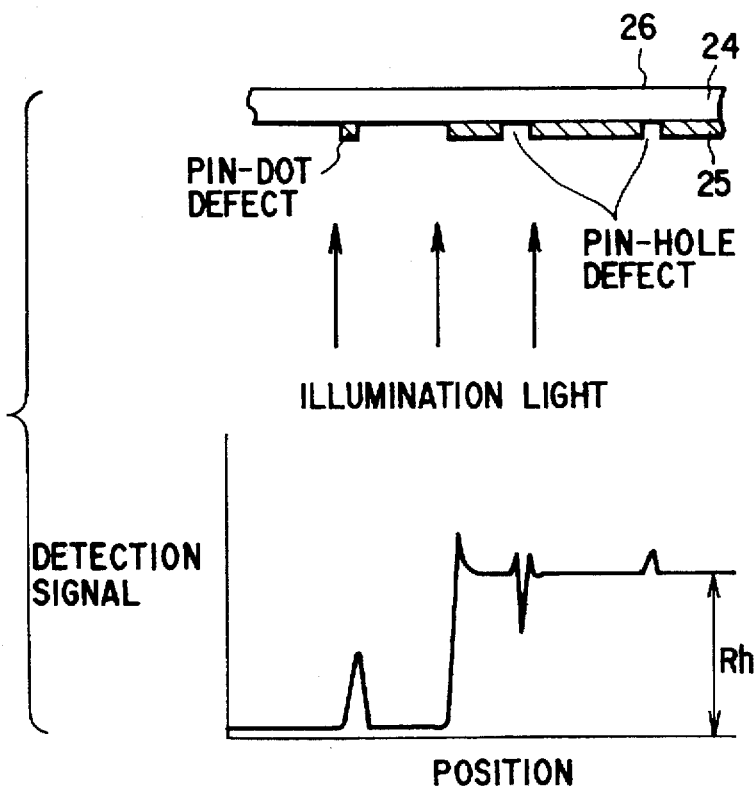

FIGS. 25A and 25B show detection signals actually obtained when observing reflection light passing through a Cr mask 23 and a phase shift mask 26 each having pin-hole defects and a pin-dot defect, illuminated with light of a wavelength different from the wavelength of the exposure light. This case is different from the former case in that the intensity of the detection signal is inverted. That is, the Cr mask 23 and the phase shift mask 26 attain an equal signal level at a glass portion as a transmit portion, but the signal level at a Cr pattern portion 22 becomes Rc. The level of Rc varies in accordance with the reflection rate of Cr with respect to the inspection wavelength. Meanwhile, the intensity of the detection signal of the phase shift mask 26 is inverted with respect to the intensity of the detection signal obtained in the former case in which the phase shift mask 26 is subjected to measurement with use of the transmitted light. The Rh signal varies in accordance with the reflection rate with respect to the inspection wavelength of the phase shifter portion 25. Therefore, although the levels may occasionally satisfy a relation of $Rh \leq Rc$, the detection signal of the phase shift mask 26 includes an overshooting portion.

As has been explained above, in a pattern defect inspection apparatus adopting the die-to-database inspection method, the signal obtained when observing a phase shift mask is greatly changed from the signal obtained when observing a Cr mask, so that the detection sensitivity is lowered and it is difficult to detect a defect.

The invention which will be explained below in more detail has an object of providing a pattern defect inspection method and an apparatus thereof which performs a defect inspection with a high sensitivity by the die-to-database inspection method, even in case of a sample such as a phase shift mask provided with a phase shifter portion.

In order to achieve the above object, in the pattern defect inspection method according to the present invention, when determining presence or absence of a pattern defect by comparing measurement pattern data obtained by detecting a pattern image formed on a sample with design pattern data used for forming the pattern, reference design pattern data obtained by making a correction in compliance with at least the characteristic of a light shielding material of the pattern formed on the sample is compared with the measurement pattern data to determine the presence or absence of a pattern defect.

Note that in the correction, an offset made so as to correspond to the obtained form of the measurement pattern data obtained and corresponding to at least the characteristic of the light shielding material is provided for the level of the data of the light shielding portion of the pattern formed on the sample among the design pattern data.

In addition, it is more preferable that in the correction, an offset made so as to correspond to the obtained form of the measurement pattern data obtained and corresponding to at least the characteristic of the light shielding material is provided for the level of the data of the light shielding portion of the pattern formed on the sample among the design pattern data, and both edge portions of a data region where the offset is provided are provided with an undershooting portion or an overshooting portion or both of the undershooting and overshooting portions, each of said undershooting portion and overshooting portion having a height and a width corresponding to the obtained form of the measurement pattern data and corresponding to at least the characteristic of the light shielding material.

In order to achieve the object described above, the pattern defect inspection apparatus according to the present invention comprises a means for converting a pattern image formed on a sample into a signal, a means for generating measurement pattern data corresponding to the pattern on the basis of the signal obtained by the converting means, a memory means for storing design pattern data used for forming the pattern, a developing means for developing the design pattern data used for forming the pattern in the form of a bit image, a processing means for performing predetermined processing on bit image data developed by the developing means, and a determination means for determining the presence or absence of a defect in a pattern formed on the sample by comparing reference data obtained through the processing means with the measurement pattern data, wherein the bit image data comprises a pattern correction means for making a correction corresponding to the obtained form of the measurement pattern data and corresponding to at least the characteristic of the light shielding material of the pattern formed on the sample, to the bit image data, and for supplying data obtained therefrom to the processing means.

Note that the pattern correction means preferably comprises a first correction means for providing an offset arranged so as to correspond to the obtained form of the measurement pattern data obtained and corresponding to at least the characteristic of the light shielding material, for the level of the data of the light shielding portion of the pattern formed on the sample among the design pattern data, and a second correction means for providing an undershooting portion or an overshooting portion, or both, of the undershooting and overshooting portions, each of said undershooting portion and overshooting portion having a height and a width corresponding to the obtained form of the measurement pattern data and corresponding to at least the characteristic of the light shielding material, for both edge portions of a data region where the offset is provided. The first and second correction means are arranged such that the correction amounts can be changed by an operation from outside.

In the inspection method and apparatus as described above, a false signal which does not originally exist in design data but occurs in a measurement signal of a phase shift mask can be generated, and therefore, the drawback that this kind of signal is detected as a defect in a conventional method and an apparatus thereof, thereby preventing an increase in the detection sensitivity, can be improved.

That is, by generating such a false signal, it is possible to provide an inspection method and an apparatus thereof which causes less false defects and improves the detection sensitivity. In other words, the defect detection sensitivity can be improved by a rate at which false defects are reduced. In addition, for example, in an inspection using transmitted light and reflection light, occurrence of overshooting or undershooting at an edge portion of the pattern described above is changed. In correspondence with the change, a false signal corresponding to an overshooting or undershooting portion of the edge portion of the pattern can be generated, and therefore, it is possible to provide a defect inspection method and an apparatus thereof which is more practical and responsible to demands from various inspections, including, an inspection using transmitted light and refection light, an inspection simultaneously detecting both of them, etc.

In the following, preferred embodiments of the present invention will be explained with reference to FIGS. 22 to 34.

Figure 26:
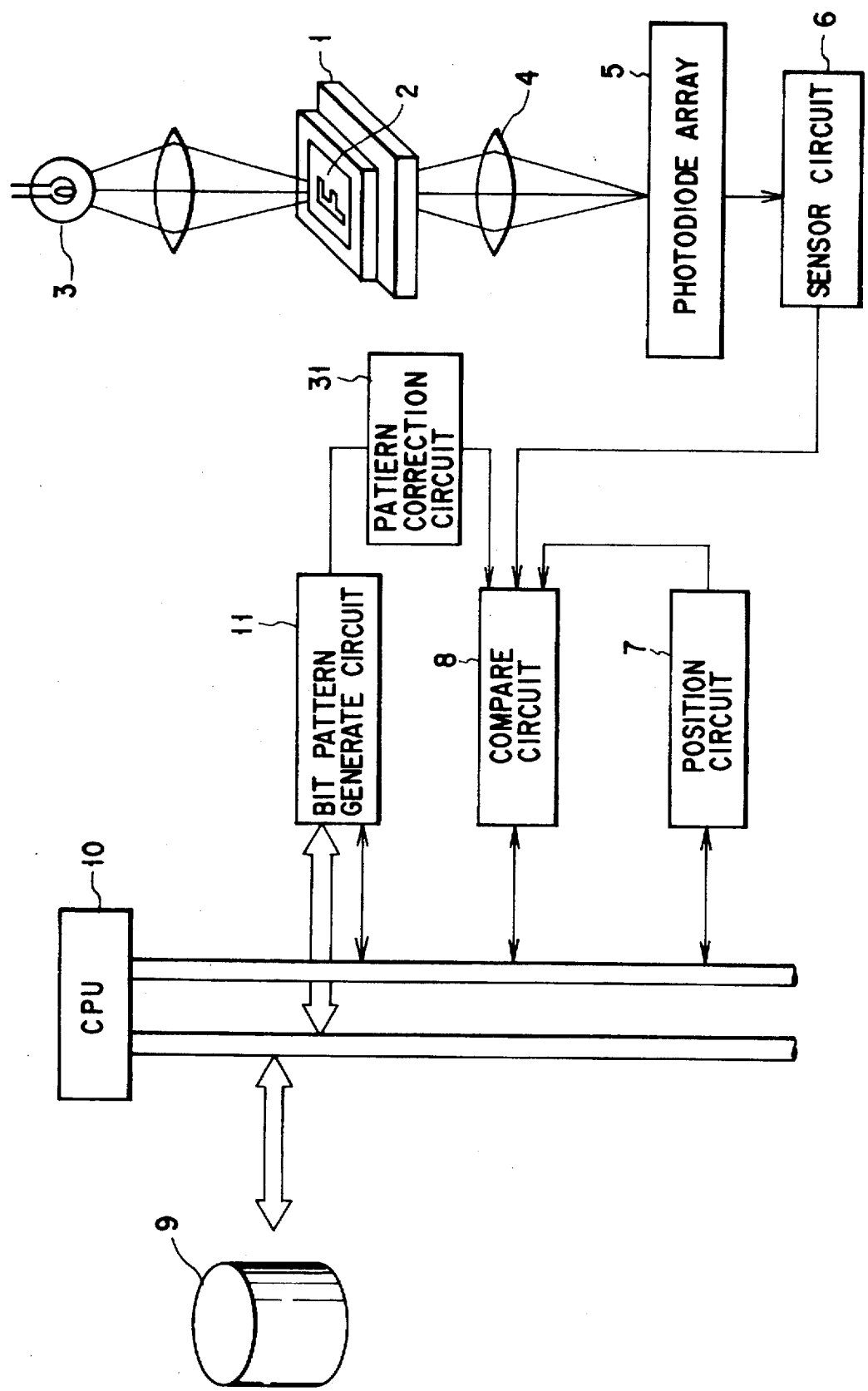
FIG. 26 schematically shows the structure of a main part of a pattern defect inspection apparatus according to another embodiment of the present invention.

FIG. 26 shows a main part of an embodiment of a pattern defect inspection apparatus for practicing the pattern defect inspection method according to the present invention.

The pattern defect inspection apparatus according to this embodiment is apparently different from conventional apparatuses in that a pattern correction circuit 31 for making correction processing to design pattern data outputted from the bit developing circuit 11 in correspondence with the type or the like of a mask to be inspected is provided between a bit developing circuit (or bit pattern generate circuit) 11 and a compare circuit 8. This pattern correction circuit 31 may include a function of the data conversion circuit 21 explained before. In exchange, the pattern correction circuit 31 and the data conversion circuit 21 may be provided between the bit developing circuit (or bit pattern generate circuit) 111 and the compare circuit 8. In the following example, explanation will be made to a case where only the pattern correction circuit 31 is provided between the bit developing circuit (or bit pattern generate circuit) 11 and the compare circuit 8.

This pattern correction circuit 31 functions in the following manner.

Here, the phase shift mask 26 of a half-tone type shown in FIG. 14B is used as a mask to be inspected, and explanation will be made to a case where the phase shift mask 26 is inspected in a transmitted light detection method. Note that the wavelength of illumination light used in the inspection is different from that of the exposure light.

Figure 27:
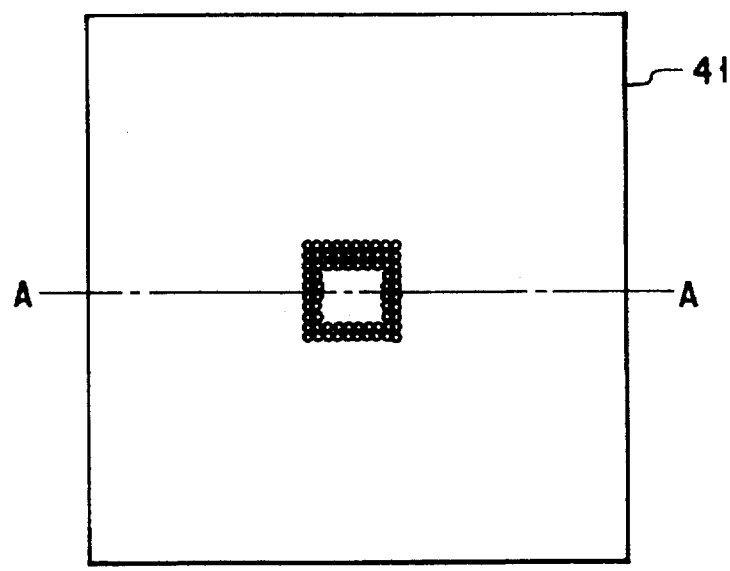
FIG. 27 is a view expressing the concept for preparing design bit image data from design pattern data.

At first, design pattern data is read from a magnetic disc 9, and then, bit image data 41 corresponding to a two-dimensional pattern image as shown in FIG. 27 is generated in a bit developing circuit 11. This kind of technique is specifically described in Japanese Patent Application KOKAI Publication 5-342308.

Figure 28A:
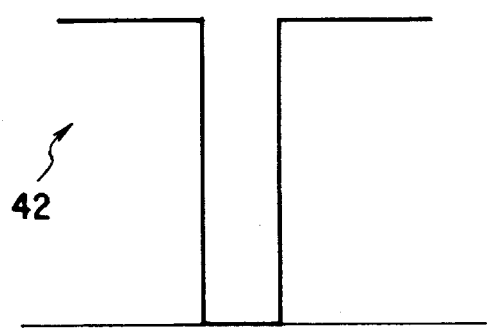
FIGS. 28A, 28B, 28C, and 28D schematically show a flow of bit image data processing when the apparatus of the embodiment is used to perform inspection according to a transmitted light detection system.

The bit size is set to values necessary for the inspection. A signal 42 corresponding to a cross-section cut along the line A—A of this image is shown in FIG. 28A. Although the signal 42 is expressed in the form of a multi-valued (gray scale valued) signal, it is assumed here that the pattern size is expressed by products obtained by multiplying the bit size by an integer, in order to simplify the explanation and that a pattern edge portion does not has an intermediate value.

The signal 42 is introduced into a correction circuit 31. The pattern correction circuit 31 performs correction processing on the signal 42 in the following manner.

At first, since a light shielding portion is set to a zero level and a transmit portion is set to a maximum level, the portion corresponding to the light shielding portion is once set to a zero level and a transmit portion is once set to a maximum level, like as in the case of the Cr mask.

Figure 28B:
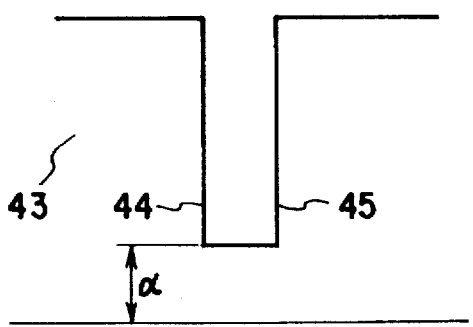

Next, as shown in FIG. 28B, an appropriate offset value α is added to the signal 42 of FIG. 28A to prepare a signal 43. This offset value a corresponds to a portion by which the signal level is increased as shown in FIG. 24B, due to an increase in the transmittance of a half-tone portion caused by observing the pattern with a wavelength different from that of the exposure light. Note that the offset value α varies, depending on the kind of the phase shift mask 26 as a mask to be inspected and the kind of material of a light shielding portion, and therefore, can be appropriately changed by an adjustment portion additionally attached to the pattern correction circuit 31.

Next, edge portions 44 and 45 of the pattern are detected. Edge detection is performed in the following manner. For example, a multi-valued signal 42 is once converted into a binary value (i.e., a value of 0 or more is converted into 1 and the other values are each converted into 0), and thereafter, scanning is performed with use of a detection mask 61 having regions A to J as shown in FIG. 32. The logic operation as shown in FIG. 33 is performed with use of data of the regions A to J in the detection mask 61, and then, such a portion which makes the output of the AND portion 52 to be "1" is determined as an edge of the pattern.

Figure 28C:
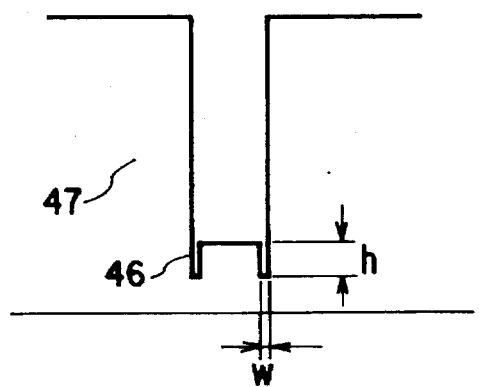

Next, on based the above results, an undershooting portion 46 having a height h and a width w is generated at a portion whose signal level is close to zero among the portions corresponding to the edge portions 44 and 45, as is shown in FIG. 28C. This undershooting portion 46 varies depending on the kind of the phase shift mask 46 to be inspected and the kind of the material of the light shielding portion, or the optical characteristic of the pattern defect inspection apparatus, and therefore, the height h and the width w can independently be changed by an adjustment portion additionally attached to the pattern correction circuit 31.

Figure 28D:
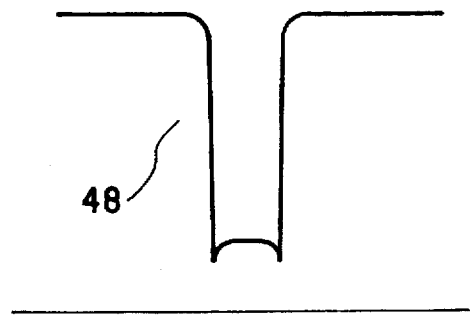

By forming such an undershooting portion 46, a design image data signal 47 similar to the detection signal of the phase shift mask 26 shown in FIG. 24B can be prepared. Thereafter, the design image data signal 47 described above is subjected to an operation convoluting filter coefficients 63 arranged in compliance with the optical characteristic, thereby to prepare a reference image data signal 48 as shown in FIG. 28D.

This reference image data signal 48 has a form substantially equal to the detection signal of an actual phase shift mask 26 shown in FIG. 24B. Further, this reference image data signal 48 is compared with an actually measured detection signal by a compare circuit 8. It is therefore possible to realize an inspection in which the detection sensitivity is improved much more than in a conventional method and an apparatus thereof.

FIG. 34 shows an operation result 64 (indicated by a continuous line) of the reference image data signal 48 prepared by the pattern correction circuit 31 and a measurement result 65 (indicated by a circle-chained line) actually measured from the phase shift mask 26. The values described in this figure are a height h and a width w used in a simulation. Thus, a design image data signal approximated to the measurement result 65 can be prepared by the pattern correction circuit 31.

As has been explained above, a pattern defect inspection adopting the die-to-database inspection method includes a reflection light detection method in which a mask to be inspected is illuminated with light having a wavelength different from the wavelength of the exposure light, and the reflection light therefrom is observed to obtain measurement data, as has been explained with reference to FIGS. 25A and 25B.

The next explanation will be made to a case in which the phase shift mask 26 shown in FIG. 25B is inspected by the reflection light detection method. Note that the wavelength of the illumination light used in this inspection is different from that of the exposure light.

First, bit image data 41 corresponding to a two-dimensional pattern image shown in FIG. 27 is prepared from the design pattern data by the bit developing circuit 11. This procedure is the same as explained in the former examples.

In the reflection light detection method, a signal must be inverted, and therefore, the pattern correction circuit 31 firstly performs white-to-black inversion of the bit image data 41. The signal 49 corresponding to an A—A cross section image of FIG. 27 is shown in FIG. 30A. Next, a portion corresponding to a light shielding portion (or phase shifter portion) is set to the maximum level, while a transmit portion is set to a level close to zero.

Next, as shown in FIG. 30B, a signal 50 is prepared by subtracting an appropriate offset value β from the maximum level of FIG. 30A. This offset value β varies depending on the kind of the phase shift mask 26 to be inspected and the kind of the material of the light shielding portion, and is therefore adjusted with use of an adjustment portion additionally added to the pattern correction circuit 31.

Next, edge portions 51 and 52 of the pattern are detected as in the former example.

Next, based on the results obtained above, an overshooting portion 53 having a height i and a width s as shown in FIG. 30C is prepared at a portion which is close to the portion which has been processed with the offset value β among the portions corresponding to the edge portions 51 and 52. This over-shooting portion 53 varies depending on the kind of the phase shift mask 26 to be inspected and the kind of the material of the light shielding portion and the optical characteristic of the apparatus, and therefore, the height i and the width s are independently adjusted by an adjustment portion additionally attached to the pattern correction circuit 31.

By forming such an overshooting portion 53, a design image data signal 54 similar to a detection signal of the phase shift mask 26 shown in FIG. 25B can be prepared. Since this design image data signal 54 is equal to a signal inverted by performing appropriate processing on the design image data signal 47 of the former example shown in FIG. 28C, this design image data signal 54 can be prepared directly from the design image data signal 47. Thereafter, the above design image data signal 54 is subjected to an operation convoluting filter coefficients shown in FIG. 63 in compliance with the optical characteristic, thereby to prepare a reference image data signal 55. Since this signal 55 is also equal to a signal inverted by performing appropriate processing on the reference image data signal 48 of the former example shown in FIG. 28D, the signal 55 may be prepared directly from the reference image data signal 48.

The reference image data signal 55 is a signal of a form substantially equal to the detection signal of an actual phase shift mask 26 shown in FIG. 25B. Further, the reference image data signal 55 is compared with a detection signal actually measured, by the compare circuit 8. It is therefore possible to perform an inspection whose detection sensitivity is much more improved than in a conventional method and an apparatus thereof.

Note that transmitted light and reflection light may simultaneously be observed in several inspection methods. The manner of performing observation with use of one equal wavelength may not be preferable, since signals then cancel each other. However, it is highly possible to change the intensities of the transmitted light and the reflection light, or to change the wavelengths of the transmitted light and the reflection light. In those cases, although signals cancel each other to some extent, the signal of only the transmitted light or only the reflection light is added to the measurement signal with a high possibility.

In general, the transmitted light is more intensive, so that an overshooting signal 56 and an undershooting signal 57, respectively occur at upper and lower portions of a pattern edge portion, as shown in FIG. 31A. Data corresponding to the overshooting and undershooting signals 56 and 57 appearing at upper and lower portions of the pattern edge portion are provided in the side of the design data 58, in form of an overshooting portion 59 with offsets α and β, a height h, and a width w and in form of an undershooting portion 60 having a height i and a width s, in the same manner as described above. Thereafter, a design image data signal extremely close to a measurement signal can be prepared by performing filter processing in the same manner as above. If differential defect detection is performed with use of the reference data thus corrected, occurrence of false defects can be reduced, resulting in an improvement in the defect detection sensitivity.

As explained above, it is desirable that another function is provided which appropriately changes the difference between a light shielding portion and a light transmit portion of the design image data signals 48 and 55 prepared from the design data, in compliance with various conditions, such as the kind of a mask to be inspected, the material of a phase shift mask, the inspection wavelength of an inspection apparatus, the optical characteristic, and the optical measurement magnification. This function is necessary for actually performing an inspection.

The above examples have been explained on a prerequisite that the exposure wavelength of light with which a phase shift mask is exposed is different from the inspection wavelength. However, recently, it has been attempted to improve the transmittance at a light shielding portion of a phase shift mask with respect to an exposure wavelength, thereby to improve the pattern transfer characteristic of the stepper. In this kind of phase shift mask, for example, the offset function using α and β as described before is required even for a pattern defect inspection apparatus in which the inspection wavelength is arranged to be equal to the exposure wavelength. Therefore, the inspection method described here is not applicable only to a case where the exposure wavelength is different from the inspection wavelength.

Various parameters described above greatly vary, depending on various conditions, e.g., the kind of a mask to be inspected, the material of a phase shift mask, the inspection wavelength of an inspection apparatus, the optical characteristic thereof, the optical measurement magnification thereof, etc. Therefore, data concerning overshooting and undershooting which should be prepared in the design data side must be freely changed in compliance with the conditions. It is therefore important to make the inspection apparatus capable of freely setting these changes.

In the case of inspecting a sample such as a phase shift mask, a portion serving as a light shielding member which completely shield light like a conventional Cr mask allows slightly light or several tens percent of light to pass, and when this portion serving as such a light shielding member is observed, overshooting and undershooting occur at edge portions in the measurement signal thereof. Since this phenomenon does not appear in CAD design data, it is necessary to artificially imitate such a phenomenon in the side of the design data in the inspection apparatus before measurement data is compared with the design data. The subject matter of the present invention is to generate such an overshooting phenomenon and an undershooting phenomenon, and the above embodiment explains merely an example of generating such overshooting and undershooting phenomena with ease. Other various methods can be considered, e.g., a means of generating these phenomena by strict optical calculations. It is needless to say that a Cr mask can be directly subjected to an inspection in case where those overshooting and undershooting portions are not prepared in the design side (although this case can be freely selected by an operator or by the apparatus). In addition, phrases of "an optical image" and "an optical characteristic" used in the present specification are not particularly important, and for example, the phrase "an optical characteristic" may be substituted by "a reflection characteristic" without problems and without changing the essential meaning of the phrase when an apparatus for observing and inspecting a pattern by injecting electron beams is used. Therefore, the application of such an apparatus is considered as not deviating the scope of the present invention.

As has been explained above, according to the present invention, for example, signals similar to overshooting and undershooting appearing in a measurement signal at a pattern edge portion specific to a phase shift mask pattern are prepared in the side of design data. Therefore, design data and measurement data of a pattern are compared with each other, thereby inspecting a defect existing in a mask with a higher detection sensitivity than in a conventional method.

In addition, for example, there are cases in which overshooting and undershooting portions at edge portions in observation signals are changed due to a phase difference between the phase of light (used in an inspection) passing through a light shielding portion of a phase shift mask and the phase of light passing through a glass portion thereof, or due to the characteristic of an optical system, e.g., the NA ratio (generally called σ) between an illumination optical system and an objective optical system, or a difference in pixel size of light receive sensors caused by changing the optical magnification. Even in those cases, the width and the height corresponding to overshooting and undershooting portions can be changed in the side of design data, so as to correspond to those changes. Therefore, the design data can be processed so as to correspond to actual measurement signals, in compliance with the structure of the phase shift mask, so that it is possible to provide a pattern defect inspection method and an inspection apparatus which respond to demands from various inspections and which are more practical.

In addition, the above invention can be applied to the invention described with reference to FIGS. 1 to 21. In this case, a data conversion circuit 21 must be provided in addition to a pattern correction circuit 31. In a method and an apparatus thereof including the data conversion circuit 21 in addition to the pattern correction circuit 31, a translucent portion of a pattern formed on a sample surface is regarded as a non-transparent portion before performing an inspection, calibration processing for adjusting the offset and gain of the sensor amplifier output is performed, and overshooting and undershooting phenomena can be generated, so that a phase shift mask can be inspected with a high accuracy.

The accompanying drawings, which are incorporated in and constitute a part of the specification, illustrate presently preferred embodiments of the invention and, together with the general description given above and the detailed description of the preferred embodiments given below, serve to explain the principles of the invention.

What is claimed is:

1. A pattern defect inspection method comprising:
   a light irradiating step of irradiating light on a sample on which a pattern is formed;
   a light receive step of receiving a pattern image of the sample obtained by light irradiation by the light irradiating step;
   an amplify step of amplifying an output from the light receive step;
   a prepare step of preparing multi-valued design pattern image data from binary design data corresponding to the pattern image of the sample;
   an offset adjust step of adjusting an offset of a light receive element amplifier, such that measurement data of a translucent portion which regards the translucent portion of the pattern formed on a surface of the sample as a non-transparent portion corresponds to design pattern image data corresponding to the translucent portion;
   a gain adjust step of adjusting a gain of the light receive element amplifier, such that measurement data of a transparent portion of the pattern formed on the sample surface corresponds to design pattern image data corresponding to the transparent portion; and an inspect step of inspecting the pattern formed on the sample surface for a defect, by comparing measurement data obtained from an output of the light receive element amplifier with design pattern image data, while the offset and gain being kept adjusted.

2. A pattern defect inspection method according to claim 1, wherein the sample is provided with a pattern consisting of a translucent region of a certain area or more and a transparent region, at least one of said offset adjust step and said gain adjust step including a step of firstly illuminating the translucent portion, while adjusting the offset of the light receive element amplifier such that the output of the light receive element amplifier obtained when thus illuminating the translucent portion is zero, and secondly illuminating the transparent portion, while adjusting the gain of the light receive element amplifier such that the output of the light receive element amplifier obtained when thus illuminating the transparent portion is a predetermined value.

3. A pattern defect inspection method according to claim 1, wherein said inspection step including a step of comparing measurement data with design pattern image data, said measurement data obtained by adding a predetermined offset amount to the output of the light receive element amplifier after the gain of the light receive element amplifier is adjusted.

4. A pattern defect inspection method according to claim 1, further comprising a step of comparing reference design pattern data obtained by making a correction to the design pattern image data, with the measurement pattern data, thereby to determine presence or absence of a pattern defect, said correction corresponding at least to a characteristic of a light shielding portion forming material of the pattern formed on the sample.

5. A pattern defect inspection method comprising:

a design pattern data providing step of providing design pattern data used for forming a mask pattern;

a measurement pattern data detecting step of detecting an image of the pattern formed on a sample, thereby to obtain measurement pattern data;

a data adjusting step of adjusting the design pattern data accordance with a characteristic of a light shielding portion of the pattern, thereby to obtain reference design pattern data; and a data comparing step of comparing the measurement pattern data with reference design pattern data, thereby to determine presence or absence of a defect in the pattern, wherein said data adjusting step includes a step of making an offset which corresponds to a form of the measurement pattern data obtained and corresponding at least to the characteristic of the light shielding portion of the pattern, and which provides a level of data of the light shielding portion of the pattern among the design pattern data.

6. A pattern defect inspection method according to claim 5, wherein said offset is included in a data region having edge portions and wherein said edge portions include at least one of an undershooting portion and an overshooting portion, each of said undershooting portion and overshooting portion having a height and a width corresponding to the obtained form of the measurement pattern data and corresponding at least to the characteristic of the light shielding material.

7. A pattern defect inspection method comprising:

a light irradiating step of irradiating light on a sample on which a pattern is formed;

a light receive step of receiving, through an optical system, a pattern image of the sample obtained by light irradiation by the light irradiating step;

an amplify step of amplifying an output from the light receive step;

an offset adjust step of adjusting an offset and a gain of a light receive element amplifier, in correspondence with a difference in an optical characteristic of the pattern formed on a surface of the sample;

a prepare step of changing a convert function in correspondence with a difference in an optical characteristic of the pattern formed on the surface of the sample, and of preparing multi-valued design pattern image data from binary design data corresponding to the pattern image of the sample, with use of the convert function; and an inspect step of inspecting the pattern formed on the sample surface for a defect, by comparing measurement data obtained from an output of the light receive element amplifier with design pattern image data.

8. A pattern defect inspection method according to claim 7, wherein the convert function of the prepare step, used for preparing multi-valued design pattern image data from binary design data, includes a function having at least three peaks when the optical characteristic of the pattern formed on the surface of the sample exhibits translucency with respect to irradiated light.

9. A pattern defect inspection method according to claim 7, further comprising a step of comparing reference design pattern data obtained by making a correction to the design pattern image data, with the measurement pattern data, thereby to determine presence or absence of a pattern defect, said correction corresponding at least to a characteristic of a light shielding portion forming material of the pattern formed on the sample.

* * * * *